(12) United States Patent
Mickelsen

(10) Patent No.: US 11,241,282 B2
(45) Date of Patent: Feb. 8, 2022

(54) METHOD AND APPARATUS FOR RAPID AND SELECTIVE TRANSURETHRAL TISSUE ABLATION

(71) Applicant: Farapulse, Inc., Menlo Park, CA (US)

(72) Inventor: Steven R. Mickelsen, Iowa City, IA (US)

(73) Assignee: Boston Scientific Scimed, Inc., Marlborough, MA (US)

( * ) Notice: Subject to any disclaimer, the term of this patent is extended or adjusted under 35 U.S.C. 154(b) by 296 days.

(21) Appl. No.: 16/595,224

(22) Filed: Oct. 7, 2019

(65) Prior Publication Data

US 2020/0038104 A1 Feb. 6, 2020

Related U.S. Application Data

(60) Division of application No. 15/354,507, filed on Nov. 17, 2016, now Pat. No. 10,433,906, which is a
(Continued)

(51) Int. Cl.
*A61B 18/14* (2006.01)
*A61B 18/12* (2006.01)
*A61B 18/00* (2006.01)

(52) U.S. Cl.
CPC ...... *A61B 18/1492* (2013.01); *A61B 18/1206* (2013.01); *A61B 2018/00029* (2013.01);
(Continued)

(58) Field of Classification Search
CPC ............ A61B 18/1206; A61B 18/1492; A61B 2018/00029; A61B 2018/00547;
(Continued)

(56) References Cited

U.S. PATENT DOCUMENTS

| 4,200,104 A | 4/1980 | Harris |
| 4,470,407 A | 9/1984 | Hussein |

(Continued)

FOREIGN PATENT DOCUMENTS

| EP | 1042990 A1 | 10/2000 |
| EP | 1125549 | 8/2001 |

(Continued)

OTHER PUBLICATIONS

Office Action for U.S. Appl. No. 16/375,561, dated Oct. 17, 2019, 15 pages.

(Continued)

*Primary Examiner* — Michael F Peffley
(74) *Attorney, Agent, or Firm* — Faegre Drinker Biddle & Reath LLP

(57) ABSTRACT

Catheter systems, tools and methods are disclosed for the selective and rapid application of DC voltage pulses to drive irreversible electroporation for minimally invasive transurethral prostate ablation. In one embodiment, a switch unit is used to modulate and apply voltage pulses from a cardiac defibrillator, while in another, the system controller can be configured to apply voltages to an independently selected multiplicity or subsets of electrodes. Devices are disclosed for more effective DC voltage application including the infusion of cooled fluid to elevate the irreversible electroporation threshold of urethral wall tissue and to selectively ablate regions of prostate tissue alone.

20 Claims, 21 Drawing Sheets

Related U.S. Application Data continuation of application No. PCT/US2015/035592, filed on Jun. 12, 2015.

(60) Provisional application No. 61/997,868, filed on Jun. 12, 2014.

(52) U.S. Cl.
CPC ............... *A61B 2018/0072* (2013.01); *A61B 2018/00547* (2013.01); *A61B 2018/00577* (2013.01); *A61B 2018/00613* (2013.01); *A61B 2018/00642* (2013.01); *A61B 2018/00702* (2013.01); *A61B 2018/00714* (2013.01); *A61B 2018/00732* (2013.01); *A61B 2018/00761* (2013.01); *A61B 2018/00767* (2013.01); *A61B 2018/00791* (2013.01); *A61B 2018/00988* (2013.01); *A61B 2018/00994* (2013.01); *A61B 2218/002* (2013.01)

(58) Field of Classification Search
CPC ........... A61B 2018/00577; A61B 2018/00613; A61B 2018/00642; A61B 2018/00702; A61B 2018/00714; A61B 2018/0072; A61B 2018/00732; A61B 2018/00761; A61B 2018/00767; A61B 2018/00791; A61B 2018/00988; A61B 2018/00994; A61B 2218/002

See application file for complete search history.

(56) References Cited

U.S. PATENT DOCUMENTS

| | | |
|---|---|---|
| 4,739,759 A | 4/1988 | Rexroth et al. |
| 5,234,004 A | 8/1993 | Hascoet et al. |
| 5,242,441 A | 9/1993 | Avitall |
| 5,257,635 A | 11/1993 | Langberg |
| 5,281,213 A | 1/1994 | Milder et al. |
| 5,304,214 A | 4/1994 | DeFord et al. |
| 5,306,296 A | 4/1994 | Wright et al. |
| 5,334,193 A | 8/1994 | Nardella |
| 5,341,807 A | 8/1994 | Nardella |
| 5,342,301 A | 8/1994 | Saab |
| 5,398,683 A | 3/1995 | Edwards et al. |
| 5,443,463 A | 8/1995 | Stern et al. |
| 5,454,370 A | 10/1995 | Avitall |
| 5,515,848 A | 5/1996 | Corbett, III et al. |
| 5,531,685 A | 7/1996 | Hemmer et al. |
| 5,545,161 A | 8/1996 | Imran |
| 5,578,040 A | 11/1996 | Smith |
| 5,617,854 A | 4/1997 | Munsif |
| 5,624,430 A | 4/1997 | Eton et al. |
| 5,667,491 A | 9/1997 | Pliquett et al. |
| 5,672,170 A | 9/1997 | Cho |
| 5,700,243 A | 12/1997 | Narciso, Jr. |
| 5,702,438 A | 12/1997 | Avitall |
| 5,706,823 A | 1/1998 | Wodlinger |
| 5,722,400 A | 3/1998 | Ockuly et al. |
| 5,722,402 A | 3/1998 | Swanson et al. |
| 5,749,914 A | 5/1998 | Janssen |
| 5,779,699 A | 7/1998 | Lipson |
| 5,788,692 A | 8/1998 | Campbell et al. |
| 5,810,762 A | 9/1998 | Hofmann |
| 5,833,710 A | 11/1998 | Jacobson |
| 5,836,874 A | 11/1998 | Swanson et al. |
| 5,836,942 A | 11/1998 | Netherly et al. |
| 5,836,947 A | 11/1998 | Fleischman et al. |
| 5,843,154 A | 12/1998 | Osypka |
| 5,849,028 A | 12/1998 | Chen |
| 5,860,974 A | 1/1999 | Abele |
| 5,863,291 A | 1/1999 | Schaer |
| 5,868,736 A | 2/1999 | Swanson et al. |
| 5,871,523 A | 2/1999 | Fleischman et al. |
| 5,876,336 A | 3/1999 | Swanson et al. |
| 5,885,278 A | 3/1999 | Fleischman et al. |
| 5,895,404 A | 4/1999 | Ruiz |
| 5,899,917 A | 5/1999 | Edwards et al. |
| 5,904,709 A | 5/1999 | Arndt et al. |
| 5,916,158 A | 6/1999 | Webster, Jr. |
| 5,916,213 A | 6/1999 | Haissaguerre et al. |
| 5,921,924 A | 7/1999 | Avitall |
| 5,928,269 A | 7/1999 | Alt |
| 5,928,270 A | 7/1999 | Ramsey, III |
| 5,938,660 A | 8/1999 | Swartz et al. |
| 6,002,955 A | 12/1999 | Willems et al. |
| 6,006,131 A | 12/1999 | Cooper et al. |
| 6,009,351 A * | 12/1999 | Flachman .......... A61B 18/1815 607/101 |
| 6,014,579 A | 1/2000 | Pomeranz et al. |
| 6,029,671 A | 2/2000 | Stevens et al. |
| 6,033,403 A | 3/2000 | Tu et al. |
| 6,035,238 A | 3/2000 | Ingle et al. |
| 6,045,550 A | 4/2000 | Simpson et al. |
| 6,068,653 A | 5/2000 | LaFontaine |
| 6,071,274 A | 6/2000 | Thompson et al. |
| 6,071,281 A | 6/2000 | Burnside et al. |
| 6,074,389 A | 6/2000 | Levine et al. |
| 6,076,012 A | 6/2000 | Swanson et al. |
| 6,090,104 A | 7/2000 | Webster, Jr. |
| 6,096,036 A | 8/2000 | Bowe et al. |
| 6,113,595 A | 9/2000 | Muntermann |
| 6,119,041 A | 9/2000 | Pomeranz et al. |
| 6,120,500 A | 9/2000 | Bednarek et al. |
| 6,142,993 A | 11/2000 | Whayne et al. |
| 6,146,381 A | 11/2000 | Bowe et al. |
| 6,164,283 A | 12/2000 | Lesh |
| 6,167,291 A | 12/2000 | Barajas et al. |
| 6,171,305 B1 | 1/2001 | Sherman |
| 6,216,034 B1 | 4/2001 | Hofmann et al. |
| 6,219,582 B1 | 4/2001 | Hofstad et al. |
| 6,223,085 B1 | 4/2001 | Dann et al. |
| 6,231,518 B1 | 5/2001 | Grabek et al. |
| 6,245,064 B1 | 6/2001 | Lesh et al. |
| 6,251,107 B1 | 6/2001 | Schaer |
| 6,251,109 B1 | 6/2001 | Asset et al. |
| 6,251,128 B1 | 6/2001 | Knopp et al. |
| 6,270,476 B1 | 8/2001 | Santoianni et al. |
| 6,272,384 B1 | 8/2001 | Simon et al. |
| 6,287,306 B1 | 9/2001 | Kroll et al. |
| 6,314,963 B1 | 11/2001 | Vaska et al. |
| 6,322,559 B1 | 11/2001 | Daulton et al. |
| 6,350,263 B1 | 2/2002 | Wetzig et al. |
| 6,370,412 B1 | 4/2002 | Armoundas et al. |
| 6,391,024 B1 | 5/2002 | Sun et al. |
| 6,447,505 B2 | 9/2002 | McGovern et al. |
| 6,464,699 B1 | 10/2002 | Swanson |
| 6,470,211 B1 | 10/2002 | Ideker et al. |
| 6,502,576 B1 | 1/2003 | Lesh |
| 6,503,247 B2 | 1/2003 | Swartz et al. |
| 6,517,534 B1 | 2/2003 | McGovern et al. |
| 6,527,724 B1 | 3/2003 | Fenici |
| 6,527,767 B2 | 3/2003 | Wang et al. |
| 6,592,581 B2 | 7/2003 | Bowe |
| 6,595,991 B2 | 7/2003 | Tollner et al. |
| 6,607,520 B2 | 8/2003 | Keane |
| 6,613,046 B1 | 9/2003 | Jenkins et al. |
| 6,623,480 B1 | 9/2003 | Kuo et al. |
| 6,638,278 B2 | 10/2003 | Falwell et al. |
| 6,666,863 B2 | 12/2003 | Wentzel et al. |
| 6,669,693 B2 | 12/2003 | Friedman |
| 6,702,811 B2 | 3/2004 | Stewart et al. |
| 6,719,756 B1 | 4/2004 | Muntermann |
| 6,723,092 B2 | 4/2004 | Brown et al. |
| 6,728,563 B2 | 4/2004 | Rashidi |
| 6,743,225 B2 | 6/2004 | Sanchez et al. |
| 6,743,226 B2 | 6/2004 | Cosman et al. |
| 6,743,239 B1 | 6/2004 | Kuehn et al. |
| 6,764,486 B2 | 7/2004 | Natale |
| 6,780,181 B2 | 8/2004 | Kroll et al. |
| 6,805,128 B1 | 10/2004 | Pless |
| 6,807,447 B2 | 10/2004 | Griffin, III |
| 6,892,091 B1 | 5/2005 | Ben-Haim et al. |
| 6,893,438 B2 | 5/2005 | Hall et al. |

(56) References Cited

U.S. PATENT DOCUMENTS

| | | |
|---|---|---|
| 6,926,714 B1 | 8/2005 | Sra |
| 6,955,173 B2 | 10/2005 | Lesh |
| 6,960,206 B2 | 11/2005 | Keane |
| 6,960,207 B2 | 11/2005 | Vanney et al. |
| 6,972,016 B2 | 12/2005 | Hill, III et al. |
| 6,973,339 B2 | 12/2005 | Govari |
| 6,979,331 B2 | 12/2005 | Hintringer et al. |
| 6,984,232 B2 | 1/2006 | Vanney et al. |
| 6,985,776 B2 | 1/2006 | Kane et al. |
| 7,001,383 B2 | 2/2006 | Keidar |
| 7,041,095 B2 | 5/2006 | Wang et al. |
| 7,113,831 B2 | 9/2006 | Hooven |
| 7,171,263 B2 | 1/2007 | Darvish et al. |
| 7,182,725 B2 | 2/2007 | Bonan et al. |
| 7,195,628 B2 | 3/2007 | Falkenberg |
| 7,207,988 B2 | 4/2007 | Leckrone et al. |
| 7,207,989 B2 | 4/2007 | Pike, Jr. et al. |
| 7,229,402 B2 | 6/2007 | Diaz et al. |
| 7,229,437 B2 | 6/2007 | Johnson et al. |
| 7,250,049 B2 | 7/2007 | Roop et al. |
| 7,285,116 B2 | 10/2007 | de la Rama et al. |
| 7,285,119 B2 | 10/2007 | Stewart et al. |
| 7,326,208 B2 | 2/2008 | Vanney et al. |
| 7,346,379 B2 | 3/2008 | Eng et al. |
| 7,367,974 B2 | 5/2008 | Haemmerich et al. |
| 7,374,567 B2 | 5/2008 | Heuser |
| 7,387,629 B2 | 6/2008 | Vanney et al. |
| 7,387,630 B2 | 6/2008 | Mest |
| 7,387,636 B2 | 6/2008 | Cohn et al. |
| 7,416,552 B2 | 8/2008 | Paul et al. |
| 7,419,477 B2 | 9/2008 | Simpson et al. |
| 7,419,489 B2 | 9/2008 | Vanney et al. |
| 7,422,591 B2 | 9/2008 | Phan |
| 7,429,261 B2 | 9/2008 | Kunis et al. |
| 7,435,248 B2 | 10/2008 | Taimisto et al. |
| 7,513,896 B2 | 4/2009 | Orszulak |
| 7,527,625 B2 | 5/2009 | Knight et al. |
| 7,578,816 B2 | 8/2009 | Boveja et al. |
| 7,588,567 B2 | 9/2009 | Boveja et al. |
| 7,623,899 B2 | 11/2009 | Worley et al. |
| 7,678,108 B2 | 3/2010 | Chrisitian et al. |
| 7,681,579 B2 | 3/2010 | Schwartz |
| 7,771,421 B2 | 8/2010 | Stewart et al. |
| 7,805,182 B2 | 9/2010 | Weese et al. |
| 7,842,031 B2 | 11/2010 | Abboud et al. |
| 7,850,642 B2 | 12/2010 | Moll et al. |
| 7,850,685 B2 | 12/2010 | Kunis et al. |
| 7,857,808 B2 | 12/2010 | Oral et al. |
| 7,857,809 B2 | 12/2010 | Drysen |
| 7,869,865 B2 | 1/2011 | Govari et al. |
| 7,896,873 B2 | 3/2011 | Hiller et al. |
| 7,917,211 B2 | 3/2011 | Zacouto |
| 7,918,819 B2 | 4/2011 | Karmarkar et al. |
| 7,918,850 B2 | 4/2011 | Govari et al. |
| 7,922,714 B2 | 4/2011 | Stevens-Wright |
| 7,955,827 B2 | 6/2011 | Rubinsky et al. |
| 8,048,067 B2 | 11/2011 | Davalos et al. |
| 8,048,072 B2 | 11/2011 | Verin et al. |
| 8,100,895 B2 | 1/2012 | Panos et al. |
| 8,100,900 B2 | 1/2012 | Prinz et al. |
| 8,108,069 B2 | 1/2012 | Stabler et al. |
| 8,133,220 B2 | 3/2012 | Lee et al. |
| 8,137,342 B2 | 3/2012 | Crossman |
| 8,145,289 B2 | 3/2012 | Calabro' et al. |
| 8,147,486 B2 | 4/2012 | Honour et al. |
| 8,160,690 B2 | 4/2012 | Wilfley et al. |
| 8,175,680 B2 | 5/2012 | Panescu |
| 8,182,477 B2 | 5/2012 | Orszulak et al. |
| 8,206,384 B2 | 6/2012 | Falwell et al. |
| 8,206,385 B2 | 6/2012 | Stangenes et al. |
| 8,216,221 B2 | 7/2012 | Ibrahim et al. |
| 8,221,411 B2 | 7/2012 | Francischelli et al. |
| 8,226,648 B2 | 7/2012 | Paul et al. |
| 8,228,065 B2 | 7/2012 | Wirtz et al. |
| 8,235,986 B2 | 8/2012 | Kulesa et al. |
| 8,235,988 B2 | 8/2012 | Davis et al. |
| 8,251,986 B2 | 8/2012 | Chornenky et al. |
| 8,282,631 B2 | 10/2012 | Davalos et al. |
| 8,287,532 B2 | 10/2012 | Carroll et al. |
| 8,414,508 B2 | 4/2013 | Thapliyal et al. |
| 8,430,875 B2 | 4/2013 | Ibrahim et al. |
| 8,433,394 B2 | 4/2013 | Harlev et al. |
| 8,449,535 B2 | 5/2013 | Deno et al. |
| 8,454,594 B2 | 6/2013 | Demarais et al. |
| 8,463,368 B2 | 6/2013 | Harlev et al. |
| 8,475,450 B2 | 7/2013 | Govari et al. |
| 8,486,063 B2 | 7/2013 | Werneth et al. |
| 8,500,733 B2 | 8/2013 | Watson |
| 8,535,304 B2 | 9/2013 | Sklar et al. |
| 8,538,501 B2 | 9/2013 | Venkatachalam et al. |
| 8,562,588 B2 | 10/2013 | Hobbs et al. |
| 8,568,406 B2 | 10/2013 | Harlev et al. |
| 8,568,410 B2 | 10/2013 | Vakharia et al. |
| 8,571,635 B2 | 10/2013 | McGee |
| 8,571,647 B2 | 10/2013 | Harlev et al. |
| 8,579,897 B2 | 11/2013 | Vakharia et al. |
| 8,585,695 B2 | 11/2013 | Shih |
| 8,588,885 B2 | 11/2013 | Hall et al. |
| 8,597,288 B2 | 12/2013 | Christian |
| 8,608,735 B2 | 12/2013 | Govari et al. |
| 8,628,522 B2 | 1/2014 | Ibrahim et al. |
| 8,632,534 B2 | 1/2014 | Pearson et al. |
| 8,647,338 B2 | 2/2014 | Chornenky et al. |
| 8,708,952 B2 | 4/2014 | Cohen et al. |
| 8,734,442 B2 | 5/2014 | Cao et al. |
| 8,771,267 B2 | 7/2014 | Kunis et al. |
| 8,795,310 B2 | 8/2014 | Fung et al. |
| 8,808,273 B2 | 8/2014 | Caples et al. |
| 8,808,281 B2 | 8/2014 | Emons et al. |
| 8,834,461 B2 | 9/2014 | Werneth et al. |
| 8,834,464 B2 | 9/2014 | Stewart et al. |
| 8,868,169 B2 | 10/2014 | Narayan et al. |
| 8,876,817 B2 | 11/2014 | Avitall et al. |
| 8,880,195 B2 | 11/2014 | Azure |
| 8,886,309 B2 | 11/2014 | Luther et al. |
| 8,903,488 B2 | 12/2014 | Callas et al. |
| 8,920,411 B2 | 12/2014 | Gelbart et al. |
| 8,926,589 B2 | 1/2015 | Govari |
| 8,932,287 B2 | 1/2015 | Gelbart et al. |
| 8,945,117 B2 | 2/2015 | Bencini |
| 8,979,841 B2 | 3/2015 | Kunis et al. |
| 8,986,278 B2 | 3/2015 | Fung et al. |
| 8,996,091 B2 | 3/2015 | de la Rama et al. |
| 9,002,442 B2 | 4/2015 | Harley et al. |
| 9,005,189 B2 | 4/2015 | Davalos et al. |
| 9,005,194 B2 | 4/2015 | Oral et al. |
| 9,011,425 B2 | 4/2015 | Fischer et al. |
| 9,044,245 B2 | 6/2015 | Condie et al. |
| 9,055,959 B2 | 6/2015 | Vaska et al. |
| 9,072,518 B2 | 7/2015 | Swanson |
| 9,078,667 B2 | 7/2015 | Besser et al. |
| 9,101,374 B1 | 8/2015 | Hoch et al. |
| 9,113,911 B2 | 8/2015 | Sherman |
| 9,119,533 B2 | 9/2015 | Ghaffari |
| 9,119,634 B2 | 9/2015 | Gelbart et al. |
| 9,131,897 B2 | 9/2015 | Harada et al. |
| 9,155,590 B2 | 10/2015 | Mathur |
| 9,162,037 B2 | 10/2015 | Belson et al. |
| 9,179,972 B2 | 11/2015 | Olson |
| 9,186,481 B2 | 11/2015 | Avitall et al. |
| 9,192,769 B2 | 11/2015 | Donofrio et al. |
| 9,204,916 B2 | 12/2015 | Lalonde |
| 9,211,405 B2 | 12/2015 | Mahapatra et al. |
| 9,216,055 B2 | 12/2015 | Spence et al. |
| 9,233,248 B2 | 1/2016 | Luther et al. |
| 9,237,926 B2 | 1/2016 | Nollert et al. |
| 9,262,252 B2 | 2/2016 | Kirkpatrick et al. |
| 9,277,957 B2 | 3/2016 | Long et al. |
| 9,282,910 B2 | 3/2016 | Narayan et al. |
| 9,289,258 B2 | 3/2016 | Cohen |
| 9,289,606 B2 | 3/2016 | Paul et al. |
| 9,295,516 B2 | 3/2016 | Pearson et al. |
| 9,301,801 B2 | 4/2016 | Scheib |
| 9,351,789 B2 | 5/2016 | Novichenok et al. |

(56) References Cited

U.S. PATENT DOCUMENTS

| | | | |
|---|---|---|---|
| 9,375,268 B2 | 6/2016 | Long | |
| 9,387,031 B2 | 7/2016 | Stewart et al. | |
| 9,414,881 B2 | 8/2016 | Callas et al. | |
| 9,468,495 B2 | 10/2016 | Kunis et al. | |
| 9,474,486 B2 | 10/2016 | Eliason et al. | |
| 9,474,574 B2 | 10/2016 | Ibrahim et al. | |
| 9,480,525 B2 | 11/2016 | Lopes et al. | |
| 9,486,272 B2 | 11/2016 | Bonyak et al. | |
| 9,486,273 B2 | 11/2016 | Lopes et al. | |
| 9,492,227 B2 | 11/2016 | Lopes et al. | |
| 9,492,228 B2 | 11/2016 | Lopes et al. | |
| 9,510,888 B2 | 12/2016 | Lalonde | |
| 9,517,103 B2 | 12/2016 | Panescu et al. | |
| 9,526,573 B2 | 12/2016 | Lopes et al. | |
| 9,532,831 B2 | 1/2017 | Reinders et al. | |
| 9,539,010 B2 | 1/2017 | Gagner et al. | |
| 9,554,848 B2 | 1/2017 | Stewart et al. | |
| 9,554,851 B2 | 1/2017 | Sklar et al. | |
| 9,700,368 B2 | 7/2017 | Callas et al. | |
| 9,724,170 B2 | 8/2017 | Mickelsen | |
| 9,757,193 B2 | 9/2017 | Zarins et al. | |
| 9,782,099 B2 | 10/2017 | Williams et al. | |
| 9,795,442 B2 | 10/2017 | Salahieh et al. | |
| 9,801,681 B2 | 10/2017 | Laske et al. | |
| 9,808,304 B2 | 11/2017 | Lalonde | |
| 9,861,802 B2 | 1/2018 | Mickelsen | |
| 9,913,685 B2 | 3/2018 | Clark et al. | |
| 9,931,487 B2 | 4/2018 | Quinn et al. | |
| 9,987,081 B1 | 6/2018 | Bowers et al. | |
| 9,999,465 B2 | 6/2018 | Long et al. | |
| 10,010,368 B2 | 7/2018 | Laske et al. | |
| 10,016,232 B1 | 7/2018 | Bowers et al. | |
| 10,130,423 B1 | 11/2018 | Viswanathan et al. | |
| 10,172,673 B2 | 1/2019 | Viswanathan et al. | |
| 10,194,818 B2 | 2/2019 | Williams et al. | |
| 10,285,755 B2 | 5/2019 | Stewart et al. | |
| 10,322,286 B2 | 6/2019 | Viswanathan et al. | |
| 10,433,906 B2 | 10/2019 | Mickelsen | |
| 10,433,908 B2 | 10/2019 | Viswanathan et al. | |
| 10,512,505 B2 | 12/2019 | Viswanathan | |
| 10,512,779 B2 | 12/2019 | Viswanathan et al. | |
| 10,517,672 B2 | 12/2019 | Long | |
| 10,617,467 B2 | 4/2020 | Viswanathan et al. | |
| 10,660,702 B2 | 5/2020 | Viswanathan et al. | |
| 2001/0000791 A1 | 5/2001 | Suorsa et al. | |
| 2001/0007070 A1 | 7/2001 | Stewart et al. | |
| 2001/0044624 A1 | 11/2001 | Seraj et al. | |
| 2002/0052602 A1 | 5/2002 | Wang et al. | |
| 2002/0058933 A1* | 5/2002 | Christopherson | A61B 18/14 606/34 |
| 2002/0077627 A1 | 6/2002 | Johnson et al. | |
| 2002/0087169 A1 | 7/2002 | Brock et al. | |
| 2002/0091384 A1 | 7/2002 | Hooven et al. | |
| 2002/0095176 A1 | 7/2002 | Liddicoat et al. | |
| 2002/0111618 A1 | 8/2002 | Stewart et al. | |
| 2002/0156526 A1 | 10/2002 | Hlavka et al. | |
| 2002/0161323 A1 | 10/2002 | Miller et al. | |
| 2002/0169445 A1 | 11/2002 | Jain et al. | |
| 2002/0177765 A1 | 11/2002 | Bowe et al. | |
| 2002/0183638 A1 | 12/2002 | Swanson | |
| 2003/0014098 A1 | 1/2003 | Quijano et al. | |
| 2003/0018374 A1 | 1/2003 | Paulos | |
| 2003/0023287 A1 | 1/2003 | Edwards et al. | |
| 2003/0028189 A1 | 2/2003 | Woloszko et al. | |
| 2003/0050637 A1 | 3/2003 | Maguire et al. | |
| 2003/0060856 A1* | 3/2003 | Chornenky | A61B 18/1492 607/40 |
| 2003/0114849 A1 | 6/2003 | Ryan | |
| 2003/0125729 A1 | 7/2003 | Hooven et al. | |
| 2003/0130598 A1 | 7/2003 | Manning et al. | |
| 2003/0130711 A1 | 7/2003 | Pearson et al. | |
| 2003/0204161 A1 | 10/2003 | Ferek Petric | |
| 2003/0229379 A1 | 12/2003 | Ramsey | |
| 2004/0039382 A1 | 2/2004 | Kroll et al. | |
| 2004/0049181 A1 | 3/2004 | Stewart et al. | |
| 2004/0049182 A1 | 3/2004 | Koblish et al. | |
| 2004/0082859 A1 | 4/2004 | Schaer | |
| 2004/0082948 A1 | 4/2004 | Stewart et al. | |
| 2004/0087939 A1 | 5/2004 | Eggers et al. | |
| 2004/0111087 A1 | 6/2004 | Stern et al. | |
| 2004/0199157 A1 | 10/2004 | Palanker et al. | |
| 2004/0231683 A1 | 11/2004 | Eng et al. | |
| 2004/0236360 A1 | 11/2004 | Cohn et al. | |
| 2004/0254607 A1 | 12/2004 | Wittenberger et al. | |
| 2004/0267337 A1 | 12/2004 | Hayzelden | |
| 2005/0033282 A1 | 2/2005 | Hooven | |
| 2005/0187545 A1 | 8/2005 | Hooven et al. | |
| 2005/0222632 A1 | 10/2005 | Obino | |
| 2005/0251130 A1 | 11/2005 | Boveja et al. | |
| 2005/0261672 A1 | 11/2005 | Deem et al. | |
| 2006/0009755 A1 | 1/2006 | Sra | |
| 2006/0009759 A1 | 1/2006 | Chrisitian et al. | |
| 2006/0015095 A1 | 1/2006 | Desinger et al. | |
| 2006/0015165 A1 | 1/2006 | Bertolero et al. | |
| 2006/0024359 A1 | 2/2006 | Walker et al. | |
| 2006/0058781 A1 | 3/2006 | Long | |
| 2006/0111702 A1 | 5/2006 | Oral et al. | |
| 2006/0142801 A1 | 6/2006 | Demarais et al. | |
| 2006/0167448 A1 | 7/2006 | Kozel | |
| 2006/0217703 A1 | 9/2006 | Chornenky et al. | |
| 2006/0241734 A1 | 10/2006 | Marshall et al. | |
| 2006/0264752 A1 | 11/2006 | Rubinsky et al. | |
| 2006/0270900 A1 | 11/2006 | Chin et al. | |
| 2006/0287648 A1 | 12/2006 | Schwartz | |
| 2006/0293730 A1 | 12/2006 | Rubinsky et al. | |
| 2006/0293731 A1 | 12/2006 | Rubinsky et al. | |
| 2007/0005053 A1 | 1/2007 | Dando | |
| 2007/0021744 A1 | 1/2007 | Creighton | |
| 2007/0060989 A1 | 3/2007 | Deem et al. | |
| 2007/0066972 A1 | 3/2007 | Ormsby et al. | |
| 2007/0129721 A1 | 6/2007 | Phan et al. | |
| 2007/0129760 A1 | 6/2007 | Demarais et al. | |
| 2007/0156135 A1 | 7/2007 | Rubinsky et al. | |
| 2007/0167740 A1 | 7/2007 | Grunewald et al. | |
| 2007/0167940 A1 | 7/2007 | Stevens-Wright | |
| 2007/0173878 A1 | 7/2007 | Heuser | |
| 2007/0208329 A1 | 9/2007 | Ward et al. | |
| 2007/0225589 A1 | 9/2007 | Viswanathan | |
| 2007/0249923 A1 | 10/2007 | Keenan | |
| 2007/0260223 A1 | 11/2007 | Scheibe et al. | |
| 2007/0270792 A1 | 11/2007 | Hennemann et al. | |
| 2008/0009855 A1 | 1/2008 | Hamou | |
| 2008/0033426 A1 | 2/2008 | Machell | |
| 2008/0065061 A1 | 3/2008 | Viswanathan | |
| 2008/0086120 A1 | 4/2008 | Mirza et al. | |
| 2008/0091195 A1 | 4/2008 | Silwa et al. | |
| 2008/0103545 A1 | 5/2008 | Bolea et al. | |
| 2008/0132885 A1 | 6/2008 | Rubinsky et al. | |
| 2008/0161789 A1 | 7/2008 | Thao et al. | |
| 2008/0172048 A1 | 7/2008 | Martin et al. | |
| 2008/0200913 A1 | 8/2008 | Viswanathan | |
| 2008/0208118 A1 | 8/2008 | Goldman | |
| 2008/0243214 A1 | 10/2008 | Koblish | |
| 2008/0281322 A1 | 11/2008 | Sherman et al. | |
| 2008/0300574 A1 | 12/2008 | Belson et al. | |
| 2008/0300588 A1 | 12/2008 | Groth et al. | |
| 2009/0024084 A1 | 1/2009 | Khosla et al. | |
| 2009/0048591 A1 | 2/2009 | Ibrahim et al. | |
| 2009/0062788 A1 | 3/2009 | Long et al. | |
| 2009/0076496 A1* | 3/2009 | Azure | A61B 18/1485 606/34 |
| 2009/0076500 A1 | 3/2009 | Azure | |
| 2009/0105654 A1 | 4/2009 | Kurth et al. | |
| 2009/0138009 A1 | 5/2009 | Viswanathan et al. | |
| 2009/0149917 A1 | 6/2009 | Whitehurst et al. | |
| 2009/0163905 A1 | 6/2009 | Winkler et al. | |
| 2009/0228003 A1 | 9/2009 | Sinelnikov | |
| 2009/0240248 A1 | 9/2009 | Deford et al. | |
| 2009/0275827 A1 | 11/2009 | Aiken et al. | |
| 2009/0281477 A1 | 11/2009 | Mikus et al. | |
| 2009/0306651 A1 | 12/2009 | Schneider | |
| 2010/0004623 A1 | 1/2010 | Hamilton et al. | |
| 2010/0023004 A1 | 1/2010 | Francischelli et al. | |
| 2010/0137861 A1 | 6/2010 | Soroff et al. | |

(56) References Cited

U.S. PATENT DOCUMENTS

| | | |
|---|---|---|
| 2010/0185140 A1 | 7/2010 | Kassab et al. |
| 2010/0185186 A1 | 7/2010 | Longoria |
| 2010/0191112 A1 | 7/2010 | Demarais et al. |
| 2010/0191232 A1 | 7/2010 | Boveda |
| 2010/0241185 A1 | 9/2010 | Mahapatra et al. |
| 2010/0261994 A1 | 10/2010 | Davalos et al. |
| 2010/0274238 A1 | 10/2010 | Klimovitch |
| 2010/0280513 A1 | 11/2010 | Juergen et al. |
| 2010/0280539 A1 | 11/2010 | Miyoshi et al. |
| 2010/0292687 A1 | 11/2010 | Kauphusman et al. |
| 2010/0312096 A1 | 12/2010 | Guttman et al. |
| 2010/0312300 A1 | 12/2010 | Ryu et al. |
| 2011/0028962 A1 | 2/2011 | Werneth et al. |
| 2011/0028964 A1 | 2/2011 | Edwards |
| 2011/0040199 A1 | 2/2011 | Hopenfeld |
| 2011/0098694 A1 | 4/2011 | Long |
| 2011/0106221 A1 | 5/2011 | Neal, II et al. |
| 2011/0130708 A1 | 6/2011 | Perry et al. |
| 2011/0144524 A1 | 6/2011 | Fish et al. |
| 2011/0144633 A1 | 6/2011 | Govari |
| 2011/0160785 A1 | 6/2011 | Mori et al. |
| 2011/0190659 A1 | 8/2011 | Long et al. |
| 2011/0190727 A1 | 8/2011 | Edmunds et al. |
| 2011/0213231 A1 | 9/2011 | Hall et al. |
| 2011/0276047 A1 | 11/2011 | Sklar et al. |
| 2011/0276075 A1 | 11/2011 | Fung et al. |
| 2011/0288544 A1 | 11/2011 | Verin et al. |
| 2011/0288547 A1 | 11/2011 | Morgan et al. |
| 2011/0313417 A1 | 12/2011 | De La Rama et al. |
| 2012/0029512 A1 | 2/2012 | Willard et al. |
| 2012/0046570 A1 | 2/2012 | Villegas et al. |
| 2012/0053581 A1 | 3/2012 | Wittkampf et al. |
| 2012/0059255 A1 | 3/2012 | Paul et al. |
| 2012/0071872 A1 | 3/2012 | Rubinsky et al. |
| 2012/0078320 A1 | 3/2012 | Schotzko et al. |
| 2012/0078343 A1 | 3/2012 | Fish |
| 2012/0089089 A1 | 4/2012 | Swain et al. |
| 2012/0095459 A1 | 4/2012 | Callas et al. |
| 2012/0101413 A1 | 4/2012 | Beetel et al. |
| 2012/0158021 A1 | 6/2012 | Morrill |
| 2012/0165667 A1 | 6/2012 | Altmann et al. |
| 2012/0172859 A1 | 7/2012 | Condie et al. |
| 2012/0172867 A1 | 7/2012 | Ryu et al. |
| 2012/0197100 A1 | 8/2012 | Razavi et al. |
| 2012/0209260 A1 | 8/2012 | Lambert et al. |
| 2012/0220998 A1 | 8/2012 | Long et al. |
| 2012/0265198 A1 | 10/2012 | Crow et al. |
| 2012/0283582 A1 | 11/2012 | Mahapatra et al. |
| 2012/0303019 A1 | 11/2012 | Zhao et al. |
| 2012/0310052 A1 | 12/2012 | Mahapatra et al. |
| 2012/0310230 A1 | 12/2012 | Willis |
| 2012/0310237 A1 | 12/2012 | Swanson |
| 2012/0316557 A1 | 12/2012 | Sartor et al. |
| 2013/0030430 A1 | 1/2013 | Stewart et al. |
| 2013/0060247 A1 | 3/2013 | Sklar et al. |
| 2013/0060248 A1 | 3/2013 | Sklar et al. |
| 2013/0079768 A1 | 3/2013 | De Luca et al. |
| 2013/0090651 A1 | 4/2013 | Smith |
| 2013/0096655 A1 | 4/2013 | Moffitt et al. |
| 2013/0103027 A1 | 4/2013 | Sklar et al. |
| 2013/0103064 A1 | 4/2013 | Arenson et al. |
| 2013/0131662 A1 | 5/2013 | Wittkampf |
| 2013/0158538 A1 | 6/2013 | Govari |
| 2013/0158621 A1 | 6/2013 | Ding et al. |
| 2013/0172715 A1 | 7/2013 | Just et al. |
| 2013/0172864 A1 | 7/2013 | Ibrahim et al. |
| 2013/0172875 A1 | 7/2013 | Govari et al. |
| 2013/0184702 A1 | 7/2013 | Neal, II et al. |
| 2013/0218157 A1 | 8/2013 | Callas et al. |
| 2013/0226174 A1 | 8/2013 | Ibrahim et al. |
| 2013/0237984 A1 | 9/2013 | Sklar |
| 2013/0253415 A1 | 9/2013 | Sano et al. |
| 2013/0296679 A1 | 11/2013 | Condie et al. |
| 2013/0310829 A1 | 11/2013 | Cohen |
| 2013/0317385 A1 | 11/2013 | Sklar et al. |
| 2013/0331831 A1 | 12/2013 | Werneth et al. |
| 2013/0338467 A1 | 12/2013 | Grasse et al. |
| 2014/0005664 A1 | 1/2014 | Govari et al. |
| 2014/0024911 A1 | 1/2014 | Harlev et al. |
| 2014/0039288 A1 | 2/2014 | Shih |
| 2014/0051993 A1 | 2/2014 | McGee |
| 2014/0052118 A1 | 2/2014 | Laske et al. |
| 2014/0052126 A1 | 2/2014 | Long et al. |
| 2014/0052216 A1 | 2/2014 | Long et al. |
| 2014/0058377 A1 | 2/2014 | Deem et al. |
| 2014/0081113 A1 | 3/2014 | Cohen et al. |
| 2014/0100563 A1 | 4/2014 | Govari et al. |
| 2014/0107644 A1 | 4/2014 | Falwell et al. |
| 2014/0142408 A1 | 5/2014 | De La Rama et al. |
| 2014/0148804 A1 | 5/2014 | Ward et al. |
| 2014/0163480 A1 | 6/2014 | Govari et al. |
| 2014/0163546 A1 | 6/2014 | Govari et al. |
| 2014/0171942 A1 | 6/2014 | Werneth et al. |
| 2014/0180035 A1 | 6/2014 | Anderson |
| 2014/0187916 A1 | 7/2014 | Clark et al. |
| 2014/0194716 A1 | 7/2014 | Diep et al. |
| 2014/0194867 A1 | 7/2014 | Fish et al. |
| 2014/0200567 A1 | 7/2014 | Cox et al. |
| 2014/0235986 A1 | 8/2014 | Harlev et al. |
| 2014/0235988 A1 | 8/2014 | Ghosh |
| 2014/0235989 A1 | 8/2014 | Wodlinger et al. |
| 2014/0243851 A1 | 8/2014 | Cohen et al. |
| 2014/0276760 A1 | 9/2014 | Bonyak et al. |
| 2014/0276782 A1 | 9/2014 | Paskar |
| 2014/0276791 A1 | 9/2014 | Ku et al. |
| 2014/0288556 A1 | 9/2014 | Ibrahim et al. |
| 2014/0303721 A1 | 10/2014 | Fung et al. |
| 2014/0343549 A1 | 11/2014 | Spear et al. |
| 2014/0364845 A1 | 12/2014 | Rashidi |
| 2014/0371613 A1 | 12/2014 | Narayan et al. |
| 2015/0005767 A1 | 1/2015 | Werneth et al. |
| 2015/0011995 A1 | 1/2015 | Avitall et al. |
| 2015/0066108 A1 | 3/2015 | Shi et al. |
| 2015/0119674 A1 | 4/2015 | Fischell et al. |
| 2015/0126840 A1 | 5/2015 | Thakur et al. |
| 2015/0133914 A1 | 5/2015 | Koblish |
| 2015/0138977 A1 | 5/2015 | Dacosta |
| 2015/0141978 A1 | 5/2015 | Subramaniam et al. |
| 2015/0141982 A1 | 5/2015 | Lee |
| 2015/0142041 A1 | 5/2015 | Kendale et al. |
| 2015/0148796 A1 | 5/2015 | Bencini |
| 2015/0150472 A1 | 6/2015 | Harlev et al. |
| 2015/0157402 A1 | 6/2015 | Kunis et al. |
| 2015/0157412 A1 | 6/2015 | Wallace et al. |
| 2015/0164584 A1 | 6/2015 | Davalos et al. |
| 2015/0173824 A1 | 6/2015 | Davalos et al. |
| 2015/0173828 A1 | 6/2015 | Avitall |
| 2015/0174404 A1 | 6/2015 | Rousso et al. |
| 2015/0182740 A1 | 7/2015 | Mickelsen |
| 2015/0196217 A1 | 7/2015 | Harlev et al. |
| 2015/0223726 A1 | 8/2015 | Harlev et al. |
| 2015/0230699 A1 | 8/2015 | Berul et al. |
| 2015/0258344 A1 | 9/2015 | Tandri et al. |
| 2015/0265342 A1 | 9/2015 | Long et al. |
| 2015/0265344 A1 | 9/2015 | Aktas et al. |
| 2015/0272656 A1 | 10/2015 | Chen |
| 2015/0272664 A9 | 10/2015 | Cohen |
| 2015/0272667 A1 | 10/2015 | Govari et al. |
| 2015/0282729 A1 | 10/2015 | Harlev et al. |
| 2015/0289923 A1 | 10/2015 | Davalos et al. |
| 2015/0304879 A1 | 10/2015 | Dacosta |
| 2015/0320481 A1 | 11/2015 | Cosman et al. |
| 2015/0321021 A1 | 11/2015 | Tandri et al. |
| 2015/0342532 A1 | 12/2015 | Basu et al. |
| 2015/0343212 A1 | 12/2015 | Rousso et al. |
| 2015/0351836 A1 | 12/2015 | Prutchi |
| 2015/0359583 A1 | 12/2015 | Swanson |
| 2016/0000500 A1 | 1/2016 | Salahieh et al. |
| 2016/0008061 A1 | 1/2016 | Fung et al. |
| 2016/0008065 A1 | 1/2016 | Gliner et al. |
| 2016/0029960 A1 | 2/2016 | Toth et al. |
| 2016/0038772 A1 | 2/2016 | Thapliyal et al. |
| 2016/0051204 A1 | 2/2016 | Harlev et al. |
| 2016/0051324 A1 | 2/2016 | Stewart et al. |

(56) References Cited

U.S. PATENT DOCUMENTS

| | | |
|---|---|---|
| 2016/0058493 A1 | 3/2016 | Neal, II et al. |
| 2016/0058506 A1 | 3/2016 | Spence et al. |
| 2016/0066993 A1 | 3/2016 | Avitall et al. |
| 2016/0074679 A1 | 3/2016 | Thapliyal et al. |
| 2016/0095531 A1 | 4/2016 | Narayan et al. |
| 2016/0095642 A1 | 4/2016 | Deno et al. |
| 2016/0095653 A1 | 4/2016 | Lambert et al. |
| 2016/0100797 A1 | 4/2016 | Mahapatra et al. |
| 2016/0100884 A1 | 4/2016 | Fay et al. |
| 2016/0106498 A1 | 4/2016 | Highsmith et al. |
| 2016/0106500 A1 | 4/2016 | Olson |
| 2016/0113709 A1 | 4/2016 | Maor |
| 2016/0113712 A1 | 4/2016 | Cheung et al. |
| 2016/0120564 A1 | 5/2016 | Kirkpatrick et al. |
| 2016/0128770 A1 | 5/2016 | Afonso et al. |
| 2016/0166167 A1 | 6/2016 | Narayan et al. |
| 2016/0166310 A1 | 6/2016 | Stewart et al. |
| 2016/0166311 A1 | 6/2016 | Long et al. |
| 2016/0174865 A1 | 6/2016 | Stewart et al. |
| 2016/0183877 A1 | 6/2016 | Williams et al. |
| 2016/0184003 A1 | 6/2016 | Srimathveeravalli et al. |
| 2016/0184004 A1 | 6/2016 | Hull et al. |
| 2016/0213282 A1 | 7/2016 | Leo et al. |
| 2016/0220307 A1 | 8/2016 | Miller et al. |
| 2016/0235470 A1 | 8/2016 | Callas et al. |
| 2016/0249972 A1 | 9/2016 | Klink |
| 2016/0256682 A1 | 9/2016 | Paul et al. |
| 2016/0287314 A1 | 10/2016 | Arena et al. |
| 2016/0310211 A1 | 10/2016 | Long |
| 2016/0324564 A1 | 11/2016 | Gerlach et al. |
| 2016/0324573 A1 | 11/2016 | Mickelsen et al. |
| 2016/0331441 A1 | 11/2016 | Konings |
| 2016/0331459 A1 | 11/2016 | Townley et al. |
| 2016/0338770 A1 | 11/2016 | Bar-Tal et al. |
| 2016/0354142 A1 | 12/2016 | Pearson et al. |
| 2016/0361109 A1 | 12/2016 | Weaver et al. |
| 2017/0001016 A1 | 1/2017 | De Ridder |
| 2017/0035499 A1 | 2/2017 | Stewart et al. |
| 2017/0042449 A1 | 2/2017 | Deno et al. |
| 2017/0042615 A1 | 2/2017 | Salahieh et al. |
| 2017/0056648 A1 | 3/2017 | Syed et al. |
| 2017/0065330 A1 | 3/2017 | Mickelsen et al. |
| 2017/0065339 A1 | 3/2017 | Mickelsen |
| 2017/0065340 A1 | 3/2017 | Long |
| 2017/0065343 A1 | 3/2017 | Mickelsen |
| 2017/0071543 A1 | 3/2017 | Basu et al. |
| 2017/0095291 A1 | 4/2017 | Harrington et al. |
| 2017/0105793 A1 | 4/2017 | Cao et al. |
| 2017/0120048 A1 | 5/2017 | He et al. |
| 2017/0146584 A1 | 5/2017 | Daw et al. |
| 2017/0151014 A1 | 6/2017 | Perfler |
| 2017/0151029 A1 | 6/2017 | Mickelsen |
| 2017/0172654 A1 | 6/2017 | Wittkampf et al. |
| 2017/0181795 A1 | 6/2017 | Debruyne |
| 2017/0189097 A1 | 7/2017 | Viswanathan et al. |
| 2017/0215953 A1 | 8/2017 | Long et al. |
| 2017/0245928 A1 | 8/2017 | Xiao et al. |
| 2017/0246455 A1 | 8/2017 | Athos et al. |
| 2017/0312024 A1 | 11/2017 | Harlev et al. |
| 2017/0312025 A1 | 11/2017 | Harlev et al. |
| 2017/0312027 A1 | 11/2017 | Harlev et al. |
| 2018/0001056 A1 | 1/2018 | Leeflang et al. |
| 2018/0028252 A1 | 2/2018 | Lalonde |
| 2018/0042674 A1 | 2/2018 | Mickelsen |
| 2018/0042675 A1 | 2/2018 | Long |
| 2018/0043153 A1 | 2/2018 | Viswanathan et al. |
| 2018/0064488 A1 | 3/2018 | Long et al. |
| 2018/0085160 A1 | 3/2018 | Viswanathan et al. |
| 2018/0093088 A1 | 4/2018 | Mickelsen |
| 2018/0133460 A1 | 5/2018 | Townley et al. |
| 2018/0161093 A1 | 6/2018 | Basu et al. |
| 2018/0168511 A1 | 6/2018 | Hall et al. |
| 2018/0184982 A1 | 7/2018 | Basu et al. |
| 2018/0193090 A1 | 7/2018 | de la Rama et al. |
| 2018/0200497 A1 | 7/2018 | Mickelsen |
| 2018/0235496 A1 | 8/2018 | Wu et al. |
| 2018/0256109 A1 | 9/2018 | Wu et al. |
| 2018/0280080 A1 | 10/2018 | Govari et al. |
| 2018/0303488 A1 | 10/2018 | Hill |
| 2018/0303543 A1 | 10/2018 | Stewart et al. |
| 2018/0311497 A1 | 11/2018 | Viswanathan et al. |
| 2018/0344202 A1 | 12/2018 | Bar-Tal et al. |
| 2018/0344393 A1 | 12/2018 | Gruba et al. |
| 2018/0360531 A1 | 12/2018 | Holmes et al. |
| 2018/0360534 A1 | 12/2018 | Teplitsky et al. |
| 2019/0015007 A1 | 1/2019 | Rottmann et al. |
| 2019/0015638 A1 | 1/2019 | Gruba et al. |
| 2019/0030328 A1 | 1/2019 | Stewart et al. |
| 2019/0046791 A1 | 2/2019 | Ebbers et al. |
| 2019/0069950 A1 | 3/2019 | Viswanathan et al. |
| 2019/0076179 A1 | 3/2019 | Babkin et al. |
| 2019/0125439 A1 | 5/2019 | Rohl et al. |
| 2019/0125788 A1 | 5/2019 | Gruba et al. |
| 2019/0143106 A1 | 5/2019 | Dewitt et al. |
| 2019/0151015 A1 | 5/2019 | Viswanathan et al. |
| 2019/0175263 A1 | 6/2019 | Altmann et al. |
| 2019/0183378 A1 | 6/2019 | Mosesov et al. |
| 2019/0183567 A1 | 6/2019 | Govari et al. |
| 2019/0192223 A1 | 6/2019 | Rankin |
| 2019/0201089 A1 | 7/2019 | Waldstreicher et al. |
| 2019/0201688 A1 | 7/2019 | Olson |
| 2019/0209235 A1 | 7/2019 | Stewart et al. |
| 2019/0223948 A1 | 7/2019 | Stewart et al. |
| 2019/0231421 A1 | 8/2019 | Viswanathan et al. |
| 2019/0231425 A1 | 8/2019 | Waldstreicher et al. |
| 2019/0254735 A1 | 8/2019 | Stewart et al. |
| 2019/0269912 A1 | 9/2019 | Viswanathan et al. |
| 2019/0298442 A1 | 10/2019 | Ogata et al. |
| 2019/0307500 A1 | 10/2019 | Byrd et al. |
| 2019/0350647 A1 | 11/2019 | Ramberg et al. |
| 2019/0350649 A1 | 11/2019 | Sutermeister et al. |
| 2020/0008869 A1 | 1/2020 | Byrd |
| 2020/0008870 A1 | 1/2020 | Gruba et al. |
| 2020/0009378 A1 | 1/2020 | Stewart et al. |
| 2020/0046423 A1 | 2/2020 | Viswanathan et al. |
| 2020/0093539 A1 | 3/2020 | Long et al. |

FOREIGN PATENT DOCUMENTS

| | | |
|---|---|---|
| EP | 0797956 | 6/2003 |
| EP | 1127552 | 6/2006 |
| EP | 1340469 | 3/2007 |
| EP | 1009303 | 6/2009 |
| EP | 2213729 | 8/2010 |
| EP | 2425871 | 3/2012 |
| EP | 1803411 | 8/2012 |
| EP | 2532320 A2 | 12/2012 |
| EP | 2587275 | 5/2013 |
| EP | 2663227 | 11/2013 |
| EP | 1909678 | 1/2014 |
| EP | 2217165 | 3/2014 |
| EP | 2376193 | 3/2014 |
| EP | 2708181 | 3/2014 |
| EP | 2777579 A1 | 9/2014 |
| EP | 2934307 | 10/2015 |
| EP | 2777585 | 6/2016 |
| EP | 2382935 B1 | 3/2018 |
| EP | 3111871 B1 | 3/2018 |
| EP | 3151773 B1 | 4/2018 |
| EP | 3056242 B1 | 7/2018 |
| JP | H06-507797 | 9/1994 |
| JP | 2000-508196 | 7/2000 |
| JP | 2005-516666 | 6/2005 |
| JP | 2006-506184 | 2/2006 |
| JP | 2008-538997 | 11/2008 |
| JP | 2009-500129 | 1/2009 |
| JP | 2011-509158 | 3/2011 |
| JP | 2012-050538 | 3/2012 |
| WO | WO 92/07622 | 5/1992 |
| WO | WO 92/21278 | 12/1992 |
| WO | WO 92/21285 | 12/1992 |
| WO | WO 94/07413 | 4/1994 |
| WO | WO 97/24073 | 7/1997 |
| WO | WO 97/25917 | 7/1997 |

(56) References Cited

FOREIGN PATENT DOCUMENTS

| WO | WO 97/37719 | 10/1997 |
|---|---|---|
| WO | WO 1999/004851 | 2/1999 |
| WO | WO 1999/022659 | 5/1999 |
| WO | WO 1999/056650 | 11/1999 |
| WO | WO 1999/059486 | 11/1999 |
| WO | WO 2002/056782 | 7/2002 |
| WO | WO 2003/053289 | 7/2003 |
| WO | WO 2003/065916 | 8/2003 |
| WO | WO 2004/045442 | 6/2004 |
| WO | WO 2004/086994 | 10/2004 |
| WO | WO 2005/046487 | 5/2005 |
| WO | WO 2006/115902 | 11/2006 |
| WO | WO 2007/006055 | 1/2007 |
| WO | WO 2007/079438 | 7/2007 |
| WO | WO 2009/082710 | 7/2009 |
| WO | WO 2009/089343 | 7/2009 |
| WO | WO 2009/137800 | 11/2009 |
| WO | WO 2010/014480 | 2/2010 |
| WO | WO 2011/028310 | 3/2011 |
| WO | WO 2011/154805 | 12/2011 |
| WO | WO 2012/051433 | 4/2012 |
| WO | WO 2012/153928 | 11/2012 |
| WO | WO 2013/019385 | 2/2013 |
| WO | WO 2014/025394 | 2/2014 |
| WO | WO 2014/031800 | 2/2014 |
| WO | WO 2014/036439 | 3/2014 |
| WO | WO 2014/160832 | 10/2014 |
| WO | WO 2015/066322 | 5/2015 |
| WO | WO 2015/099786 | 7/2015 |
| WO | WO 2015/103530 | 7/2015 |
| WO | WO 2015/103574 | 7/2015 |
| WO | WO 2015/130824 | 9/2015 |
| WO | WO 2015/140741 | 9/2015 |
| WO | WO 2015/143327 | 9/2015 |
| WO | WO 2015/171921 | 11/2015 |
| WO | WO 2015/175944 | 11/2015 |
| WO | WO 2015/192018 | 12/2015 |
| WO | WO 2015/192027 | 12/2015 |
| WO | WO 2016/059027 | 4/2016 |
| WO | WO 2016/060983 | 4/2016 |
| WO | WO 2016/081650 | 5/2016 |
| WO | WO 2016/090175 | 6/2016 |
| WO | WO 2017/093926 | 6/2017 |
| WO | WO 2017/119934 | 7/2017 |
| WO | WO 2017/120169 | 7/2017 |
| WO | WO 2017/192477 | 11/2017 |
| WO | WO 2017/192495 | 11/2017 |
| WO | WO 2017/201504 | 11/2017 |
| WO | WO 2017/218734 | 12/2017 |
| WO | WO 2018/005511 | 1/2018 |
| WO | WO 2018/106569 | 6/2018 |
| WO | WO 2018/200800 | 11/2018 |
| WO | WO 2019/023259 | 1/2019 |
| WO | WO 2019/023280 | 1/2019 |
| WO | WO 2019/035071 | 2/2019 |
| WO | WO 2019/133606 | 7/2019 |
| WO | WO 2019/133608 | 7/2019 |
| WO | WO 2019/136218 | 7/2019 |
| WO | WO 2019/181612 | 9/2019 |
| WO | WO 2019/234133 | 12/2019 |

OTHER PUBLICATIONS

Office Action for U.S. Appl. No. 16/595,250, dated Mar. 16, 2020, 7 pages.
International Search Report and Written Opinion for International Application No. PCT/US2019/051998, dated Feb. 26, 2020, 11 pages.
Partial Supplementary European Search Report for European Application No. 13827672.0, dated Mar. 23, 2016, 6 pages.
Supplementary European Search Report for European Application No. 13827672.0, dated Jul. 11, 2016, 12 pages.
Office Action for European Application No. 13827672.0, dated Feb. 5, 2018, 6 pages.
Notice of Reasons for Rejection for Japanese Application No. 2015-526522, dated Mar. 6, 2017, 3 pages.
Office Action for U.S. Appl. No. 14/400,455, dated Mar. 30, 2017, 10 pages.
International Search Report and Written Opinion for International Application No. PCT/US2013/031252, dated Jul. 19, 2013, 12 pages.
Office Action for U.S. Appl. No. 15/819,726, dated Jun. 4, 2018, 17 pages.
Office Action for U.S. Appl. No. 15/917,194, dated Jun. 4, 2018, 17 pages.
Office Action for U.S. Appl. No. 15/917,194, dated Oct. 9, 2018, 13 pages.
First Office Action for Chinese Application No. 201580006848.8, dated Jan. 29, 2018, 15 pages.
Office Action for U.S. Appl. No. 15/201,997, dated Dec. 17, 2018, 17 pages.
International Search Report and Written Opinion for International Application No. PCT/US2018/050660, dated Nov. 26, 2018, 13 pages.
Office Action for European Application No. 15701856.5, dated Dec. 11, 2017, 6 pages.
Notice of Reasons for Rejection for Japanese Application No. 2016-544072, dated Oct. 1, 2018, 11 pages.
International Search Report and Written Opinion for International Application No. PCT/US2015/010138, dated Mar. 26, 2015, 14 pages.
International Preliminary Reporton Patentability for International Application No. PCT/US2015/010138, dated Jul. 12, 2016, 9 pages.
Supplementary European Search Report for European Application No. 15733297.4, dated Aug. 10, 2017, 7 pages.
Office Action for U.S. Appl. No. 15/201,997, dated Apr. 3, 2017, 6 pages.
Office Action for U.S. Appl. No. 15/201,997, dated Aug. 29, 2017, 12 pages.
Office Action for U.S. Appl. No. 15/201,997, dated Jul. 12, 2018, 12 pages.
International Search Report and Written Opinion for International Application No. PCT/US2015/010223, dated Apr. 10, 2015, 19 pages.
International Preliminary Reporton Patentability for International Application No. PCT/US2015/010223, dated Jul. 12, 2016, 12 pages.
International Search Report and Written Opinion for International Application No. PCT/US2015/029734, dated Nov. 24, 2015, 15 pages.
Office Action for U.S. Appl. No. 15/795,062, dated Dec. 19, 2017, 14 pages.
Office Action for U.S. Appl. No. 15/795,062, dated Apr. 9, 2018, 20 pages.
International Search Report and Written Opinion for International Application No. PCT/US2015/031086, dated Oct. 21, 2015, 16 pages.
Office Action for U.S. Appl. No. 15/795,075, dated Feb. 6, 2018, 9 pages.
Office Action for U.S. Appl. No. 15/795,075, dated Jun. 15, 2018, 10 pages.
Extended European Search Report for European Application No. 15849844.4, dated May 3, 2018, 8 pages.
International Search Report and Written Opinion for International Application No. PCT/US2015/055105, dated Mar. 1, 2016, 15 pages.
Office Action for U.S. Appl. No. 15/796,255, dated Jan. 10, 2018, 12 pages.
Extended European Search Report for European Application No. 15806855.1, dated Jan. 3, 2018, 8 pages.
International Search Report and Written Opinion for International Application No. PCT/US2015/035582, dated Oct. 2, 2015, 17 pages.
Extended European Search Report for European Application No. 15806278.6, dated Feb. 9, 2018, 5 pages.

(56) References Cited

OTHER PUBLICATIONS

International Search Report and Written Opinion for International Application No. PCT/US2015/035592, dated Oct. 2, 2015, 13 pages.
Office Action for U.S. Appl. No. 15/334,646, dated Jul. 25, 2017, 19 pages.
Office Action for U.S. Appl. No. 15/334,646, dated Nov. 16, 2017, 26 pages.
International Search Report and Written Opinion for International Application No. PCT/US2016/057664, dated Feb. 24, 2017, 11 pages.
Office Action for U.S. Appl. No. 15/796,375, dated Jan. 24, 2018, 25 pages.
Office Action for U.S. Appl. No. 15/796,375, dated May 30, 2018, 26 pages.
Office Action for U.S. Appl. No. 15/796,375, dated Nov. 16, 2018, 27 pages.
International Search Report and Written Opinion for International Application No. PCT/US2017/012099, dated May 18, 2017, 17 pages.
Office Action for U.S. Appl. No. 15/711,266, dated Feb. 23, 2018, 14 pages.
International Search Report and Written Opinion for International Application No. PCT/US2018/029938, dated Aug. 29, 2018, 14 pages.
International Search Report and Written Opinion for International Application No. PCT/US2017/037609, dated Nov. 8, 2017, 13 pages.
Office Action for U.S. Appl. No. 15/672,916, dated Feb. 13, 2018, 16 pages.
Office Action for U.S. Appl. No. 15/672,916, dated Jul. 20, 2018, 23 pages.
Office Action for U.S. Appl. No. 15/499,804, dated Jan. 3, 2018, 20 pages.
Office Action for U.S. Appl. No. 15/794,717, dated Feb. 1, 2018, 10 pages.
International Search Report and Written Opinion for International Application No. PCT/US2018/029552, dated Jun. 29, 2018, 13 pages.
Office Action for U.S. Appl. No. 15/970,404, dated Oct. 9, 2018, 21 pages.
du Pre, B.C. et al., "Minimal coronary artery damage by myocardial electroporation ablation," Europace, 15(1):144-149 (2013).
Hobbs, E. P., "Investor Relations Update: Tissue Ablation via Irreversible Electroporation (IRE)," Powerpoint (2004), 16 pages.
Lavee, J. et al., "A Novel Nonthermal Energy Source for Surgical Epicardial Atrial Ablation: Irreversible Electroporation," The Heart Surgery Forum #2006-1202, 10(2), 2007 [Epub Mar. 2007].
Madhavan, M. et al., "Novel Percutaneous Epicardial Autonomic Modulation in the Canine for Atrial Fibrillation: Results of an Efficacy and Safety Study," Pace, 00:1-11 (2016).
Neven, K. et al., "Safety and Feasibility of Closed Chest Epicardial Catheter Ablation Using Electroporation," Circ Arrhythm Electrophysiol., 7:913-919 (2014).
Neven, K. et al., "Myocardial Lesion Size After Epicardial Electroporation Catheter Ablation After Subxiphoid Puncture," Circ Arrhythm Electrophysiol., 7(4):728-733 (2014).
Neven, K. et al., "Epicardial linear electroporation ablation and lesion size," Heart Rhythm, 11:1465-1470 (2014).
van Driel, V.J.H.M. et al., "Pulmonary Vein Stenosis After Catheter Ablation Electroporation Versus Radiofrequency," Circ Arrhythm Electrophysiol., 7(4):734-738 (2014).
van Driel, V.J.H.M. et al., "Low vulnerability of the right phrenic nerve to electroporation ablation," Heart Rhythm, 12:1838-1844 (2015).
Wittkampf, F.H. et al., "Myocardial Lesion Depth With Circular Electroporation Ablation," Circ. Arrhythm Electrophysiol., 5(3):581-586 (2012).
Wittkampf, F.H. et al., "Feasibility of Electroporation for the Creation of Pulmonary Vein Ostial Lesions," J Cardiovasc Electrophysiol, 22(3):302-309 (Mar. 2011).
Office Action for Canadian Application No. 2,881,462, dated Mar. 19, 2019, 5 pages.
Office Action for Japanese Application No. 2018-036714, dated Jan. 16, 2019, 8 pages.
Office Action for U.S. Appl. No. 15/201,983, dated Apr. 3, 2019, 16 pages.
Office Action for U.S. Appl. No. 15/341,523, dated Jan. 29, 2019, 10 pages.
Office Action for U.S. Appl. No. 15/795,075, dated Apr. 10, 2019, 11 pages.
Office Action for U.S. Appl. No. 15/672,916, dated Apr. 9, 2019, 31 pages.
Partial European Search Report for European Application No. 18170210.1, dated Feb. 14, 2019, 13 pages.
Office Action for U.S. Appl. No. 15/970,404, dated Apr. 12, 2019, 20 pages.
Office Action for U.S. Appl. No. 15/917,194, dated Apr. 29, 2019, 10 pages.
Office Action for U.S. Appl. No. 15/795,062, dated May 3, 2019, 21 pages.
International Search Report and Written Opinion for International Application No. PCT/US2019/014226, dated Apr. 29, 2019, 15 pages.
Extended European Search Report for European Application No. 18189811.5, dated May 14, 2019, 7 pages.
International Search Report and Written Opinion for International Application No. PCT/US2019/017322, dated May 10, 2019, 15 pages.
Office Action for U.S. Appl. No. 15/341,512, dated Aug. 1, 2019, 19 pages.
Office Action for U.S. Appl. No. 15/341,523, dated Jul. 30, 2019, 8 pages.
Office Action for U.S. Appl. No. 15/795,075, dated Jul. 31, 2019, 12 pages.
Office Action for U.S. Appl. No. 15/484,969, dated Sep. 4, 2019, 12 pages.
Office Action for U.S. Appl. No. 15/354,475, dated May 23, 2019, 7 pages.
Extended European Search Report for European Application No. 16884132.8, dated Jul. 8, 2019, 7 pages.
Office Action for U.S. Appl. No. 16/416,677, dated Aug. 15, 2019, 8 pages.
Extended European Search Report for European Application No. 17736218.3 dated Aug. 23, 2019, 9 pages.
Office Action for U.S. Appl. No. 16/181,027, dated Sep. 4, 2019, 12 pages.
Office Action for U.S. Appl. No. 16/240,066, dated May 29, 2019, 7 pages.
Extended European Search Report for European Application No. 18170210.1, dated May 17, 2019, 11 pages.
International Search Report and Written Opinion for International Application No. PCT/US2019/030922, dated Sep. 6, 2019, 12 pages.
International Search Report and Written Opinion for International Application No. PCT/US2019/030882, dated Sep. 10, 2019, 17 pages.
Office Action for U.S. Appl. No. 16/405,515, dated Sep. 6, 2019, 9 pages.
International Search Report and Written Opinion for International Application No. PCT/US2019/031135, dated Aug. 5, 2019, 11 pages.
International Search Report and Written Opinion for International Application No. PCT/US2019/028943, dated Sep. 17, 2019, 17 pages.

* cited by examiner

METHOD AND APPARATUS FOR RAPID AND SELECTIVE TRANSURETHRAL TISSUE ABLATION

CROSS-REFERENCE TO RELATED APPLICATIONS

This application is a divisional of U.S. patent application Ser. No. 15/354,507, titled "METHOD AND APPARATUS FOR RAPID AND SELECTIVE TRANSURETHRAL TISSUE ABLATION," filed Nov. 17, 2016, now U.S. Pat. No. 10,433,906, which is a continuation of PCT Application No. PCT/US2015/035592, titled "METHOD AND APPARATUS FOR RAPID AND SELECTIVE TRANSURETHRAL TISSUE ABLATION," filed Jun. 12, 2015, which claims the benefit of priority to U.S. Provisional Application Ser. No. 61/997,868, titled "METHOD AND APPARATUS FOR RAPID AND SELECTIVE TRANSURETHRAL TISSUE ABLATION," filed Jun. 12, 2014, the entire disclosures of which are incorporated herein by reference in their entirety.

BACKGROUND

The embodiments described herein relate generally to medical devices for therapeutic electrical energy delivery, and more particularly to the surgical specialty of urology. Specifically, systems and methods for delivering electrical energy in the context of ablating tissue rapidly and selectively in minimally invasive transurethral clinical therapies by the application of suitably timed pulsed voltages that generate irreversible electroporation of cell membranes. Such irreversible electroporation can possibly be generated in conjunction with the application of disclosed means of enhancing electroporation efficacy.

Transurethral resection of the prostate (TURP) remains the gold standard for treating benign prostatic hypertrophy (BPH). Alternatives to surgical resection are ablation of tissues using thermal-based destruction of tissue using multiple forms of energy (laser, microwave, radiofrequency ablation etc.). The most common postoperative complication with known transurethral procedures is urethral stricture, occurring in approximately 4.4% of patients overall. Furthermore known transurethral procedures indiscriminately resect or ablate urethral epithelium in the process of de-bulking the prostate tissues. The urethral injury contributes to the recovery time and morbidity of the acute procedure.

In the past decade or two the technique of electroporation has advanced from the laboratory to clinical applications, while the effects of brief pulses of high voltages and large electric fields on tissue has been investigated for the past forty years or more. It has been known that the application of brief high DC voltages to tissue, thereby generating locally high electric fields typically in the range of hundreds of Volts/centimeter can disrupt cell membranes by generating pores in the cell membrane. While the precise mechanism of this electrically-driven pore generation or electroporation is not well understood, it is thought that the application of relatively large electric fields generates instabilities in the lipid bilayers in cell membranes, causing the occurrence of a distribution of local gaps or pores in the membrane. If the applied electric field at the membrane is larger than a threshold value, the electroporation is irreversible and the pores remain open, permitting exchange of material across the membrane and leading to apoptosis or cell death. Subsequently the tissue heals in a natural process.

Historically, known direct current ablation techniques were pioneered in cardiovascular catheter-based ablation. More recently these techniques have been applied for the treatment of solid tumors with a clinical tool that employed very short impulses. The application of known ablation techniques to solid tumors on other applications, however, has not included selectively targeting tissue for irreversible electroporation ablation. Specifically, tissue susceptibility to irreversible cell injury from strong brief pulses of electricity depends on a number of important variables. Factors include: cell size, geometry, and orientation within the electric field, the constitution of the cell membrane and organelles, and local temperature. While pulsed DC voltages are known to drive electroporation under the right circumstances, the examples of electroporation applications in medicine and delivery methods described in the prior art do not discuss specificity and rapidity of action.

Thus, there is a need for selective energy delivery for electroporation and its modulation in various tissue types as well as pulses that permit rapid action and completion of therapy delivery. There is also a need for more effective generation of voltage pulses and control methods, as well as appropriate devices or tools addressing a variety of specific clinical applications, particularly in minimally invasive applications. Such more selective and effective electroporation delivery methods can broaden the areas of clinical application of electroporation including therapeutic treatment of a variety of cardiac arrhythmias, tissue ablation, and transurethral applications.

SUMMARY

The embodiments described herein address the need for tools and methods for rapid and selective application of irreversible electroporation therapy as well as pulse generation and methods in the context of transurethral applications such as in the minimally invasive treatment of benign prostate hyperplasia. In some embodiments [FILL IN]

DETAILED DESCRIPTION

Figure 1A:
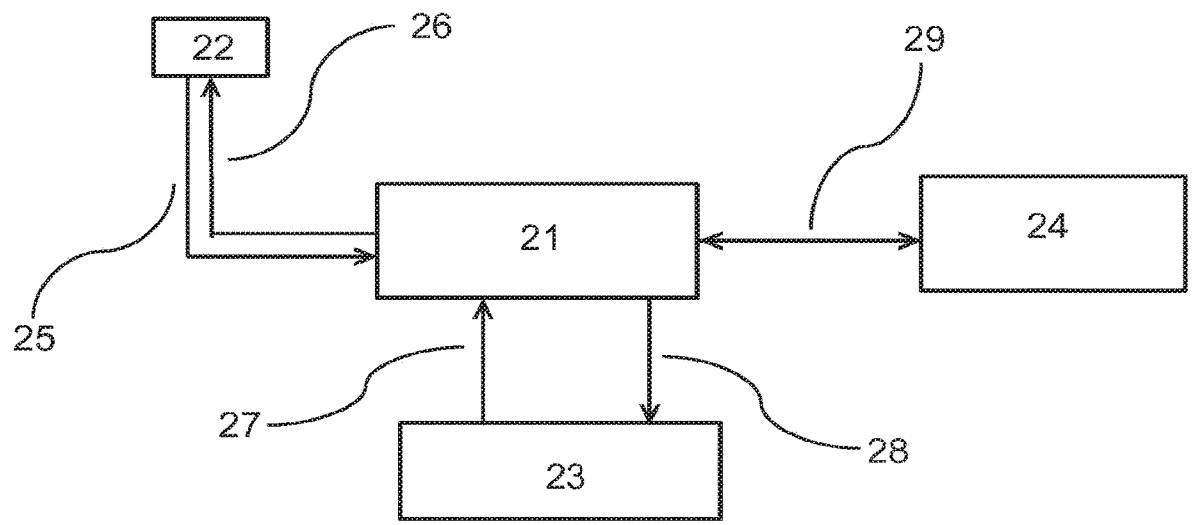
FIG. 1A is a schematic illustration of an irreversible electroporation system that includes a DC voltage/signal generator, a controller unit that is configurable to apply voltages to selected subsets of electrodes with independent subset selections for anode and cathode and that is connected to a computer, and one or more medical devices connected to the controller.

Systems and methods for electroporation to ablate enlarged prostate tissue in a selective fashion are described herein. The embodiments described herein result in well-controlled and specific delivery of electroporation in an efficacious manner. Specifically, the systems and methods described herein produced the desired results while ensuring at the same time that delicate epithelial tissue in and around the urethral wall is not damaged.

The embodiments described herein account for the differences in irreversible ablation threshold by creating a local temperature gradient that protects urethral epithelium (cooling it to raise the threshold electric field for ablation) and heating the target prostate tissue (warming it to make it more susceptible to ablation). In this manner, the targeted prostate tissue can be selectively ablated while leaving the urethra intact and unaffected. As described above, strong exogenous electrical fields can ablate tissue without significantly disrupting the extracellular matrix. The inflammatory response is relatively modest when compared to ablation from thermal injury. The proposed prostate ablation system exploits the tissue-specific susceptibility differences between the transitional epithelial cells of the urethra and the prostate tissue In some embodiments, an apparatus includes an electrode controller configured to be operably coupled to a voltage pulse generator and a catheter. The voltage pulse generator is configured to produce a pulsed voltage waveform. The catheter includes a plurality of electrodes. The electrode controller is implemented in at least one of a memory or a processor, and includes a feedback module, a thermal control module and a pulse delivery module. The feedback module is configured to determine a temperature of a target tissue. The thermal control module is configured to produce a signal to control a cooling fluid to the catheter based on the temperature of the target tissue. The pulse delivery module is configured to deliver an output signal associated with the pulsed voltage waveform to the plurality of electrodes, and is further configured to shunt an excess current associated with the pulsed voltage waveform In some embodiments, an apparatus includes an electrode controller configured to be operably coupled to a voltage pulse generator, a catheter and a heater. The voltage pulse generator is configured to produce a pulsed voltage waveform. The catheter includes a plurality of electrodes. The electrode controller is implemented in at least one of a memory or a processor, and includes a thermal control module and a pulse delivery module. The thermal control module is configured to produce a first signal to control a cooling fluid to the catheter. The thermal control module is configured to produce a second signal to control a temperature of a heater. The pulse delivery module configured to deliver an output signal associated with the pulsed voltage waveform to the plurality of electrodes. The pulse delivery module is further configured to shunt an excess current associated with the pulsed voltage waveform.

In some embodiments, a method includes receiving, at a feedback module of an electrode controller, a temperature signal associated with a temperature of a urethral wall against which a medical a catheter is disposed. The catheter includes a plurality of electrodes. A control signal based on the temperature signal is delivered to a cooling unit to produce a flow of cooling fluid to the catheter. An output signal associated with a pulsed voltage waveform is delivered to the plurality of electrodes.

In some embodiments, a non-transitory processor readable medium storing code representing instructions to be executed by a processor includes code to cause the processor to receive a temperature signal associated with a temperature of a urethral wall against which a medical a catheter is disposed. The medical catheter including a plurality of electrodes. The code further includes code to produce a control signal to a cooling unit to produce a flow of cooling fluid to the catheter. The control signal based on the temperature signal. The code further includes code to deliver an output signal associated with the pulsed voltage waveform to the plurality of electrodes when the target tissue is at the target temperature.

In some embodiments, a system includes a pulse generator unit, a controller unit, a flexible medical device and a fluid pump. The pulse generator unit is configured to produce a pulsed voltage waveform. The controller unit is connected to the pulse generator unit, and is configured to modulate pulses from the generator unit. The controller unit includes shunt circuitry configured to shunt excess current. The controller unit includes a thermal control module. The flexible medical device includes a plurality of electrodes and defines a series of ports through which a cooling fluid can flow. The flexible medical device is configured to be connected to the controller unit such that a voltage signal associated with the pulsed voltage waveform can be conveyed to the plurality of electrodes. The fluid pump is configured to produce the cooling flow in response to a cooling signal produced by the thermal control module of the controller unit. In some embodiments, the system optionally includes a trans-rectal probe including a probe head having a heater. The heater is configured to heat a portion of a prostate tissue in response to a cooling signal produced by the thermal control module of the controller unit.

In some embodiments, a system or method includes the use of temperature to selectively ablate tissue as the threshold of irreversible electroporation is temperature-dependent, for example with the use of pulses of cold fluid irrigation in the form of saline fluid. In this manner, epithelial tissue in the region of the urethral wall can be left intact, while at the same time the ablation is effectively applied only to deeper tissue structures adjacent to the urethral wall. The delivery of cold fluid can be suitably pulsed in order to ensure that only epithelial tissue is cooled while deeper tissue is not substantively cooled. Surprisingly, in some embodiments, the pulses of fluid flow can involve periodical infusions of warm fluid in time intervals between voltage pulses. In one embodiment, the control of fluid pulse and temperature parameters is also programmable.

In some embodiments, the temperature of the transurethral probe can be modulated by other suitable methods such as a closed-loop coolant, thermoelectric transduction, and/or resistive heating coils. A trans-rectal probe could be added to the apparatus to accentuate the delivery of thermal energy (radiant heat, infrared, microwave, ultrasound etc.). Using a two-probe technique the rectal probe could be arranged as a dedicated heating probe and the intraurethral device as a dedicated cooling source.

The timing and intensity of thermal delivery are delivered in a manner to optimize the local tissue thermal environment. The goal is to maximally cool the tissues of the urethra and bladder that would be exposed to the ablation impulse while warming the targeted tissues of the prostate. The most direct way to achieve this is to start the cycle with warm irrigation or radiant energy to allow heat transfer into the surrounding prostate tissues followed by a short phase of cooling. The longer first phase would produce a relative steady state increase in the prostate tissue above the normal body temperature but not high enough to cause thermal tissue injury. The second, shorter phase delivers cooling to the local urethra and bladder in such a way as to quickly drop the local tissue temperature below normal body temperature. The ablation impulse would be delivered into tissue with a thermal gradient favoring preservation of the epithelial urethra while increasing susceptibility of the prostate tissues.

In some embodiments, an irreversible electroporation system is disclosed that includes a DC voltage/signal generator and a controller. Further, the controller is capable of applying control inputs with possibly programmable voltage pulse parameters as well as programmable selection of electrodes as cathodes or anodes. The generator can output waveforms that can be selected to generate a sequence of voltage pulses in either monophasic or biphasic forms and with either constant or progressively changing amplitudes. Methods of control and DC voltage application from a generator capable of selective excitation of sets of electrodes are disclosed.

In some embodiments, a method includes the treatment of benign prostatic hyperplasia. In one embodiment, a standard defibrillator can be utilized together with a switch to selectively apply a portion of the voltage pulse generated by the defibrillator unit, while excessive current is shunted away with a suitable shunt circuit.

The cooling irrigation fluid for any of the devices, systems and methods described herein can be any biocompatible fluid. In some embodiments, the current transfer properties of the fluid are of significant importance, and thus the irrigation fluid is formulated to facilitate the methods described herein. The irrigation used in the cooling phase can have a high electrolyte content (normal saline for example) with the possible inclusion of other biocompatible compounds to facilitate ablation and reduce local injury.

In some embodiments, the irreversible electroporation system described herein includes a DC voltage/signal generator and a controller unit for applying voltage pulses to electrodes. In one embodiment, the signal generator is capable of being configured to apply voltages to a selected multiplicity or a subset of electrodes on a transurethral minimally invasive catheter device. The controller is additionally capable of being programmable for voltage pulse parameters. In one embodiment where the device through which voltage pulses are applied also carries cooled fluid, the controller unit can also control fluid flow or pulse rate and fluid temperature.

The DC voltage is applied in brief pulses sufficient to cause irreversible electroporation and can be in the range of 0.5 kV to 10 kV and more preferably in the range 1 kV to 2.5 kV, so that a threshold electric field value in the range of 200-1000 Volts/cm is effectively achieved in the prostate tissue to be ablated. In one embodiment, the DC voltage value is selected directly by a user from a suitable dial, slider, touch screen, or any other user interface. The DC voltage pulse also results in a current flowing between the anode and cathode electrodes in the distal region of the catheter device that is inserted into the patient urethra, with the current entering the prostate tissue from the anode(s) and returning back through the cathode electrodes. The forward and return current paths (leads) are both inside the catheter. Areas of prostate tissue where the electric field is sufficiently large for irreversible electroporation are ablated during the DC voltage pulse application.

As used in this specification, the singular forms "a," "an" and "the" include plural referents unless the context clearly dictates otherwise. Thus, for example, the term "a member" is intended to mean a single member or a combination of members, "a material" is intended to mean one or more materials, "a processor" is intended to mean a single processor or multiple processors; and "memory" is intended to mean one or more memories, or a combination thereof.

As used herein, the terms "about" and "approximately" generally mean plus or minus 10% of the value stated. For example, about 0.5 would include 0.45 and 0.55, about 10 would include 9 to 11, about 1000 would include 900 to 1100.

A schematic diagram of the electroporation system according to an embodiment in one embodiment is shown in FIG. 1A. A DC voltage/signal generator 23 is driven by a controller unit 21 that interfaces with a computer device 24 by means of a two-way communication link 29. The controller can perform channel selection and routing functions for applying DC voltages to appropriate electrodes that have been selected by a user or by the computer 24, and apply the voltages via a multiplicity of leads (shown collectively as 26) to a catheter device 22. The catheter device 22, and any of the catheter devices described herein can be similar to the ablation catheters described in PCT Publication No. WO2014/025394, entitled "Catheters, Catheter Systems, and Methods for Puncturing Through a Tissue Structure," filed on Mar. 14, 2013 ("the '394 PCT Application), which is incorporated herein by reference in its entirety.

Some leads from the controller 21 could also carry control signals to drive pulsatile fluid flow through the device and/or for fluid temperature control (not shown). The catheter device can also possibly send back information such as temperature data from other sensors back to the controller 21 as indicated by the data stream 25, possibly on separate leads. While the DC voltage generator 23 sends a DC voltage to the controller 21 through leads 27, the voltage generator is driven by control and timing inputs 28 from the controller unit 21. Multiple DC voltage pulses can be applied in a pulse train to ensure that sufficient tissue ablation has occurred. Further, the user can repeat the delivery of irreversible electroporation over several distinct pulse trains for further confidence.

Figure 1B:
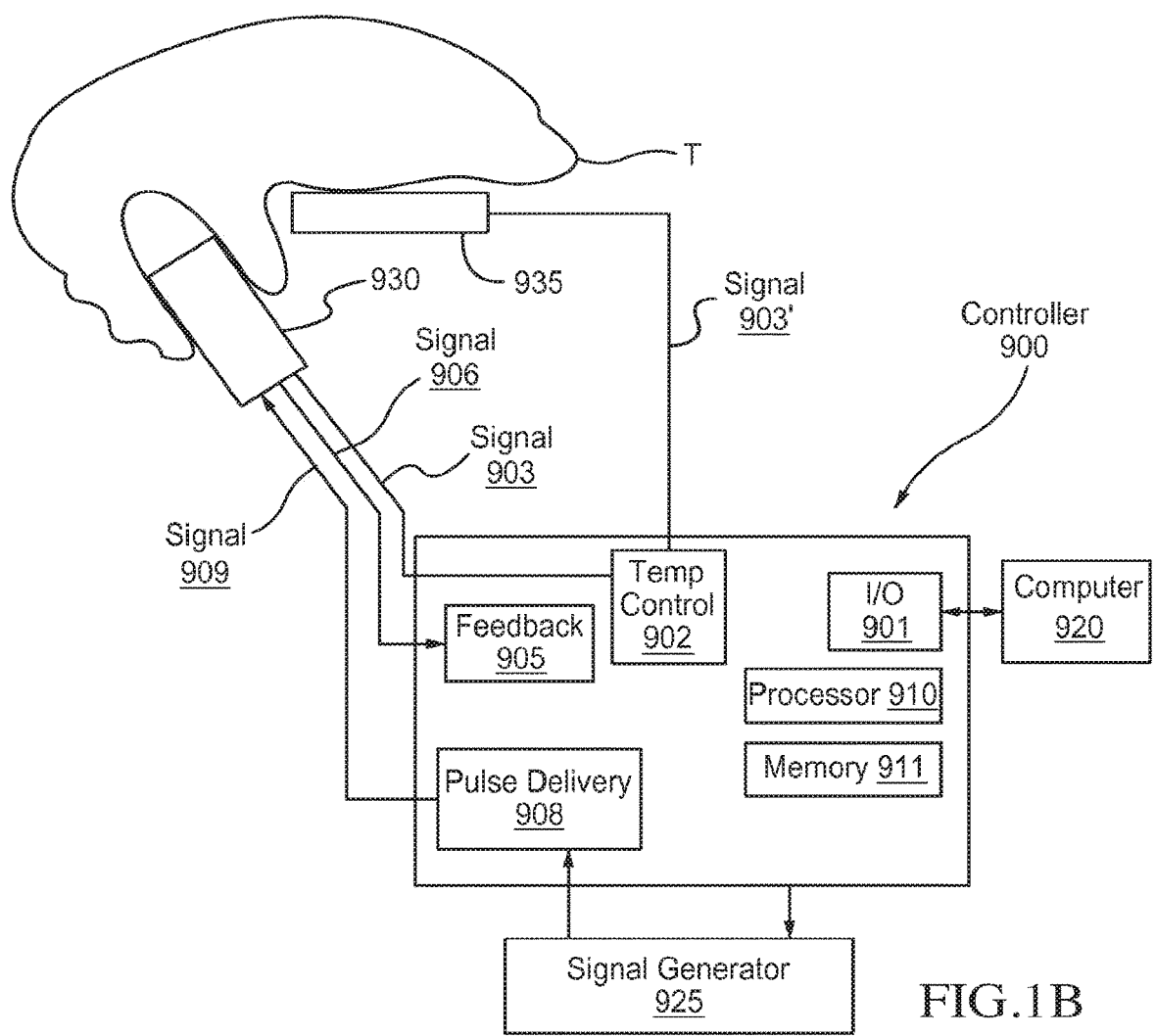
FIG. 1B is a schematic illustration of an irreversible electroporation system that includes a DC voltage/signal generator and a controller according to an embodiment.

In some embodiments, the electrode controller can include one or more modules and can automatically control the flow of fluid through a catheter (e.g., to produce a pulsed flow or the like), control heating of a particular portion of target tissue (e.g., the prostate), adjust a characteristic of the voltage waveform, or the like. For example, FIG. 1B shows an electroporation system according to an embodiment that includes an electrode controller 900 and a signal generator 925. In some embodiments, the signal generator 925 can be a cardiac defibrillator device. The electrode controller 900 is coupled to a computer 920 or other input/output device, and is configured to be operably coupled to a medical device 930. The medical device 930 can be one or more of the catheters of the types shown and described herein. Further the medical device 930 can be coupled to, disposed about and/or in contact with a target tissue T. For example, in some embodiments, the medical device can be disposed within a urethra of a patient. In this manner, as described herein, the electroporation system, including the electrode controller 900 and the signal generator 925, can deliver voltage pulses to the target tissue for therapeutic purposes.

Moreover, in some embodiments, the electrode controller 900 is optionally configured to be operably coupled to a medical device 935 that is distinct from the medical device 930. For example, the electrode controller 900 can optionally be coupled to a trans-rectal probe that includes a mechanism for delivering heat to a portion of the target tissue (e.g., the prostate).

The controller 900 can include a memory 911, a processor 910, and an input/output module (or interface) 901. The controller 900 can also include a temperature control module 902, a feedback module 905, and a pulse delivery module 908. The electrode controller 900 is coupled to a computer 920 or other input/output device via the input/output module (or interface) 901.

The processor 910 can be any processor configured to, for example, write data into and read data from the memory 911, and execute the instructions and/or methods stored within the memory 911. Furthermore, the processor 910 can be configured to control operation of the other modules within the controller (e.g., the temperature control module 902, the feedback module 905, and the pulse delivery module 908). Specifically, the processor 910 can receive a signal including user input, temperature data, distance measurements or the like and determine a set of electrodes to which voltage pulses should be applied, the desired timing and sequence of the voltage pulses and the like. In other embodiments, the processor 910 can be, for example, an application-specific integrated circuit (ASIC) or a combination of ASICs, which are designed to perform one or more specific functions. In yet other embodiments, the microprocessor can be an analog or digital circuit, or a combination of multiple circuits.

The memory device 911 can be any suitable device such as, for example, a read only memory (ROM) component, a random access memory (RAM) component, electronically programmable read only memory (EPROM), erasable electronically programmable read only memory (EEPROM), registers, cache memory, and/or flash memory. Any of the modules (the temperature control module 902, the feedback module 905, and the pulse delivery module 908) can be implemented by the processor 910 and/or stored within the memory 911.

As shown, the electrode controller 900 operably coupled to the signal generator 925. In some embodiments, the signal generator can be a cardiac defibrillator. The signal generator includes circuitry, components and/or code to produce a series of DC voltage pulses for delivery to electrodes included within the medical device 930. For example, in some embodiments, the signal generator 925 can be configured to produce a biphasic waveform having a pre-polarizing pulse followed by a polarizing pulse. The signal generator 925 can be any suitable signal generator of the types shown and described herein.

The pulse delivery module 908 of the electrode controller 900 includes circuitry, components and/or code to deliver an output signal associated with the pulsed voltage waveform produced by the signal generator 925. This signal (shown as signal 909) can be any signal of the types shown and described herein, and can be of a type and/or have characteristics to be therapeutically effective. In some embodiments, the pulse delivery module 908 receives input from other portions of the system, and can therefore send the signal 909 to the appropriate subset of electrodes, as described herein.

The electrode controller 900 includes the temperature control module 902. The temperature control module 902 includes circuitry, components and/or code to produce a control signal (identified as signal 903) that can be delivered to the device 935 and/or a control signal (identified as signal 903') that can be delivered to either a coolant supply (not shown) or to the medical device 930. In this manner, the temperature control module 902 can facilitate heating of a first portion of the tissue (e.g., via the device 935) and/or cooling of a second portion of the tissue T (e.g., the urethral walls).

In some embodiment, the ablation controller and signal generator can be mounted on a rolling trolley, and the user can control the device using a touchscreen interface that is in the sterile field. The touchscreen can be for example an LCD touchscreen in a plastic housing mountable to a standard medical rail or post and can be used to select the electrodes for ablation and to ready the device to fire. The interface can for example be covered with a clear sterile plastic drape. In one embodiment, the operator can select the electrodes involved in the voltage pulse delivery. For example, in one embodiment the operator can select electrodes from the touchscreen with appropriate graphical buttons. In one embodiment, the ablation pulse train can be initiated by holding down a hand-held trigger button that is in the sterile field, possibly with the pulse train parameters (such as for example individual pulse parameters, number of pulses in the pulse train) having been programmed. The hand-held trigger button can be illuminated red to indicate that the device is "armed" and ready to ablate. The trigger button can be compatible for use in a sterile field and when attached to the controller can be illuminated a different color, for example white. When the device is firing, the trigger button flashes in sequence with the pulse delivery in a specific color such as red. The waveform of each delivered pulse is displayed on the touchscreen interface. While a touchscreen interface is one embodiment, other user interfaces can be used by a user to control the system such as for example a graphical display on a laptop or monitor display controlled by a standard computer mouse or joystick.

In some embodiments, the system (generator and controller) according to an embodiment can deliver rectangular-wave pulses with a peak maximum voltage of about 5 kV into a load with an impedance in the range of 30 Ohm to 3000 Ohm for a maximum duration of 200 µs, with a 100 µs maximum duration being still more preferred. Pulses can be delivered in a multiplexed and synchronized manner to a multi-electrode catheter inside the body with a duty cycle of up to 50% (for short bursts). The pulses can generally be delivered in bursts, such as for example a sequence of between 2 and 10 pulses interrupted by pauses of between 1 ms and 1000 ms. The multiplexer controller is capable of running an automated sequence to deliver the impulses/impulse trains (from the DC voltage signal/impulse generator) to the tissue target within the body. The controller system is capable of switching between subsets/nodes of electrodes located on the single use catheter.

Figure 2:
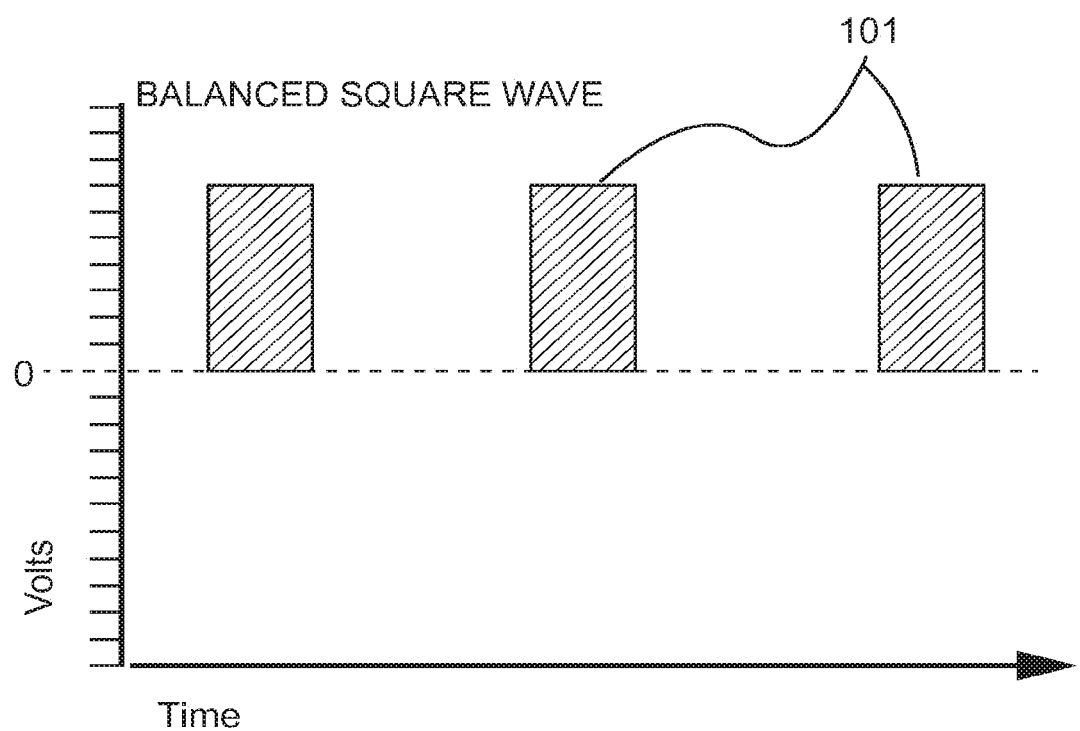
FIG. 2 is a schematic illustration of a waveform generated by the irreversible electroporation system according to an embodiment, showing a balanced square wave.
Figure 3:
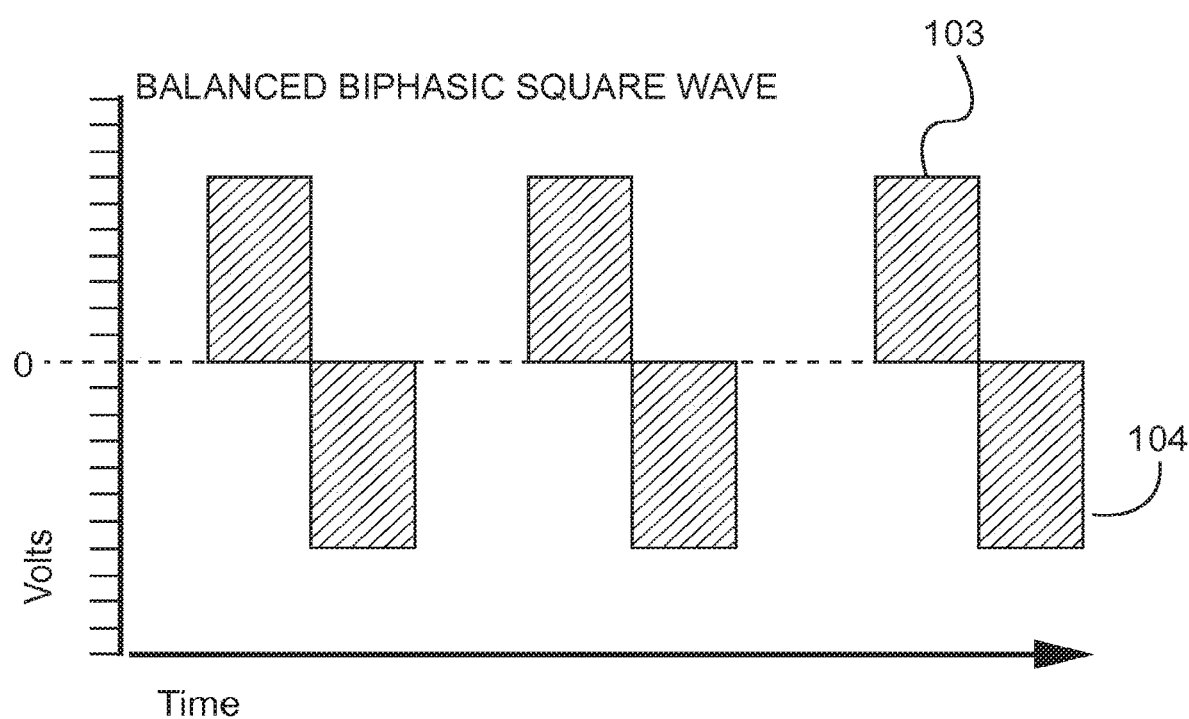
FIG. 3 is a schematic illustration of a waveform generated by the irreversible electroporation system according to an embodiment, showing a balanced biphasic square wave.

The controllers and generators described herein can output waveforms that can be selected to generate a sequence of voltage pulses in either monophasic or biphasic forms and with either constant or progressively changing amplitudes. FIG. 2 shows a rectangular wave pulse train where the pulses 101 have a uniform height or maximum voltage. FIG. 3 shows an example of a balanced biphasic rectangular pulse train, where each positive voltage pulse such as 103 is immediately followed by a negative voltage pulse such as 104 of equal amplitude and opposite sign. While in this example the biphasic pulses are balanced with equal amplitudes of the positive and negative voltages, in other embodiments an unbalanced biphasic waveform could also be used as may be convenient for a given application. In some embodiments, generally biphasic voltage pulses are utilized to drive irreversible electroporation ablation in prostate tissue with the device and system of the present disclosure.

Figure 4:
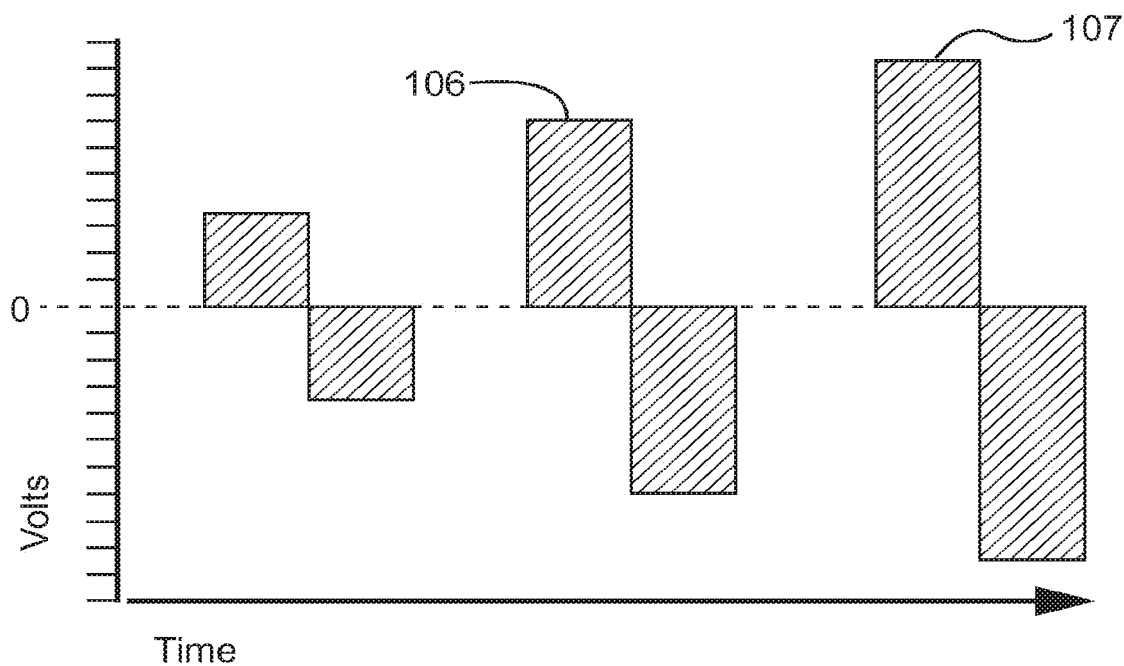
FIG. 4 is a schematic illustration of a waveform generated by the irreversible electroporation system according to an embodiment, showing a progressive balanced biphasic square wave.

Yet another example of a waveform or pulse shape that can be generated by the system is illustrated in FIG. 4, which shows a progressive balanced rectangular pulse train, where each distinct biphasic pulse has equal-amplitude positive and negative voltages, but each pulse such as 107 is larger in amplitude than its immediate predecessor 106. Other variations such as a progressive unbalanced rectangular pulse train, or indeed a wide variety of other variations of pulse amplitude with respect to time can be conceived and implemented by those skilled in the art based on the teachings herein.

The time duration of each irreversible electroporation rectangular voltage pulse could lie in the range from 1 nanosecond to 10 milliseconds, with the range 10 microseconds to 1 millisecond being more preferable and the range 50 microseconds to 300 microseconds being still more preferable. The time interval between successive pulses of a pulse train could be in the range of 10 microseconds to 1 millisecond, with the range 50 microseconds to 300 microseconds being more preferable. The number of pulses applied in a single pulse train (with delays between individual pulses lying in the ranges just mentioned) can range from 1 to 100, with the range 1 to 10 being more preferable. As described in the foregoing, a pulse train can be driven by a user-controlled switch or button, in one embodiment preferably mounted on a hand-held joystick-like device. In one mode of operation a pulse train can be generated for every push of such a control button, while in an alternate mode of operation pulse trains can be generated with a pre-determined delay between successive pulse trains, for as long as the user-controlled switch or button is engaged by the user.

Figure 5:
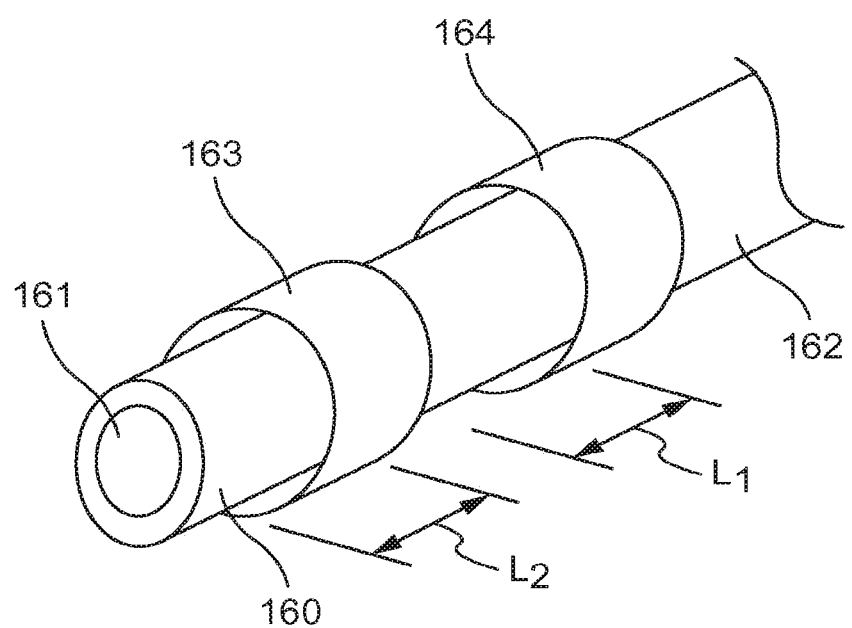
FIG. 5 is a schematic illustration of a distal portion of a catheter according to an embodiment, showing two distal electrodes and a lumen for transfer of fluid through the catheter.

A catheter device for distal ablation with the electroporation system according to an embodiment is shown schematically in FIG. 5. The ablation catheter with shaft 162 has two electrodes disposed in the distal section of the catheter, with a relatively proximally placed electrode 164 of length $L_1$ exposed on the catheter shaft and a relatively distally placed electrode 163 of length $L_2$ also exposed on the catheter shaft. The catheter shaft is made of a material with high dielectric strength such as for example a polymer comprising Teflon. Both electrodes are metallic, and in one embodiment the anode could be poly-metallic in construction, for example comprising regions of Titanium and regions of Platinum. The catheter has a lumen shown as 161 and in one embodiment the distal tip portion 160 could have a diameter that is smaller than that at the relatively proximal shaft section 162, so that the tip is tapered, making for easier insertion into the urethra. In one embodiment the electrode lengths $L_1$ and $L_2$ could be different, while in an alternate embodiment they are closely similar in length. The catheter is inserted via the urethra and positioned with its distal portion abutting prostate tissue in the region of which tissue ablation is desired.

Figure 6:
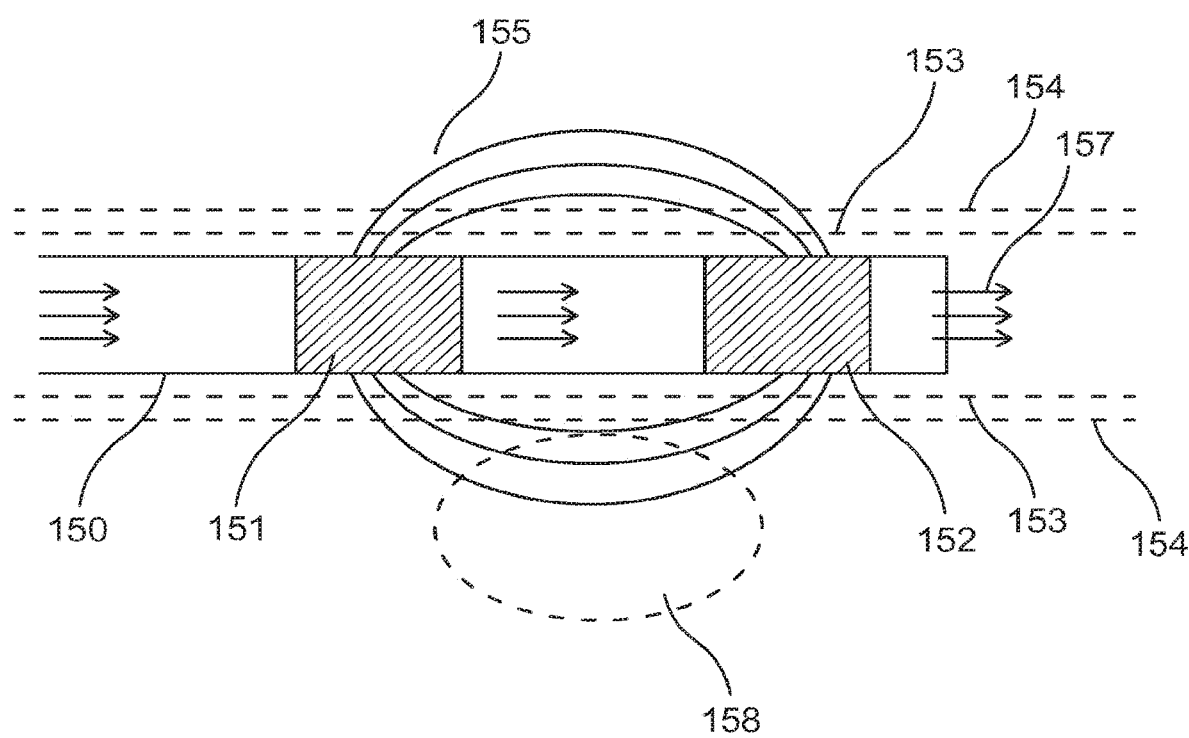
FIG. 6 is a schematic illustration of a distal portion of a catheter according to an embodiment in a tubular anatomy, where two electrodes with the roles of cathode and anode are shown, along with a schematic depiction of the electric field in the region between the electrodes.

FIG. 6 schematically illustrates a catheter device with shaft 150 and distal electrodes 151 and 152 disposed longitudinally in a urethral vessel in a prostate tissue region, with urethral walls indicated by dashed lines, with inner vessel wall 153 and outer vessel wall 154 respectively. Thus the layer of tissue between lines 153 and 154 is epithelial tissue, while the tissue outside the outer vessel wall is prostate tissue in this schematic depiction. When the electrodes are activated with a voltage applied across them, an electric field is generated in the region around and between the electrodes, depicted schematically by field lines 155 in FIG. 6. In some embodiments, the catheter lumen carries a fluid flow of cooled fluid depicted by arrows 157; the fluid can be for instance a saline fluid which is harmlessly disposed of by the body. The temperature of the saline fluid can be about 55 degrees Fahrenheit or lower.

In some embodiments, the time for which a cold temperature is maintained at the patient contacting catheter surface is monitored and varied, so that the cooling control is applied in time in a pulse-like format. This is done in order to maintain a surface layer of tissue at a suitably low or cold temperature, while ensuring that deeper regions of tissue undergo no more than marginal cooling. For example, the thermal diffusivity D of skin tissue is known to be in the range of 0.11 mm$^2$/s. From standard heat diffusion theory, in a time T the depth x to which a temperature change applied at the surface is propagated is given (in two dimensions) by x~$\sqrt{2DT}$. Thus, in 20 seconds of cooling, the depth x would be approximately 2 mm, which is about the thickness of skin tissue. In one mode of operation of the system according to an embodiment, the cooling of the electrodes is performed in discrete time intervals in the range of 10 seconds to 40 seconds, followed by a pulse train application, the entire duration of the pulse train being in the range of less than about 8 seconds. Thus, the application of cooling could also be performed in pulses.

The urethral wall tissue in the region between dashed lines 153 and 154 in FIG. 6 is then always at a cold temperature during voltage pulse application. This increases its irreversible electroporation threshold, thereby maintaining its integrity with no ablation occurring in this zone. At the same time prostate tissue beyond the urethral wall, for example in the region denoted 158 in FIG. 6, undergoes irreversible electroporation due to the sufficiently large electric fields in this region. The next ablation in the same tissue region is performed, if necessary, after another cooling pulse is applied over a discrete time interval, and so on. In one method according to an embodiment, a heating pulse could follow a cooling pulse in order to ensure that the temperature in the interior of the tissue does not fall below a threshold value. Suitably cold saline could generally be infused in small quantities in each pulse, for example at a rate in the range of a few milliliters/second or less.

Figure 7:
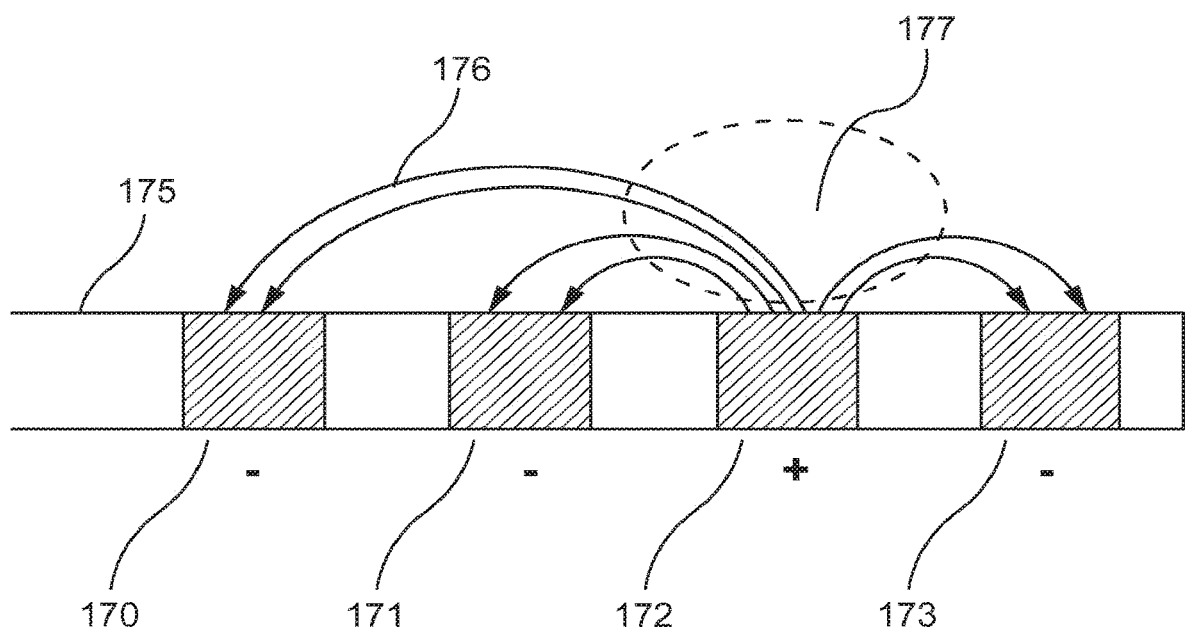
FIG. 7 is a schematic illustration of a distal portion of a catheter according to an embodiment, where multiple electrodes are shown with their various respective roles of anodes or cathodes, along with a schematic depiction of the electric field in the regions between the electrodes.

FIG. 7 schematically depicts one embodiment of the transurethral catheter device according to an embodiment with multiple electrodes in its distal region. In this example, the catheter shaft 175 has four electrodes 170, 171, 172 and 173 disposed in its distal region. With electrode 172 chosen as anode and the other electrodes as cathodes, with an applied voltage the resulting electric field lines are indicated schematically by 176. The resulting electric field intensity would be locally high in the approximate region schematically shown as the region 177 inside the dashed-line ellipse, and this would serve as a selected zone of ablation. It should be clear that by choosing different electrodes or electrode combinations as anodes or cathodes, the desired zone of ablation can be varied. In one embodiment, as before, the catheter can have a lumen carrying a pulsed flow of cold fluid in order to increase the electroporation threshold of the urethral wall. In this manner, tissue outside the urethral wall can be selectively ablated while leaving the urethral wall itself unaffected. In one embodiment the catheter device can have at least one temperature sensor such as a thermistor or thermocouple disposed in the distal portion of the device for monitoring temperature.

Figure 8:
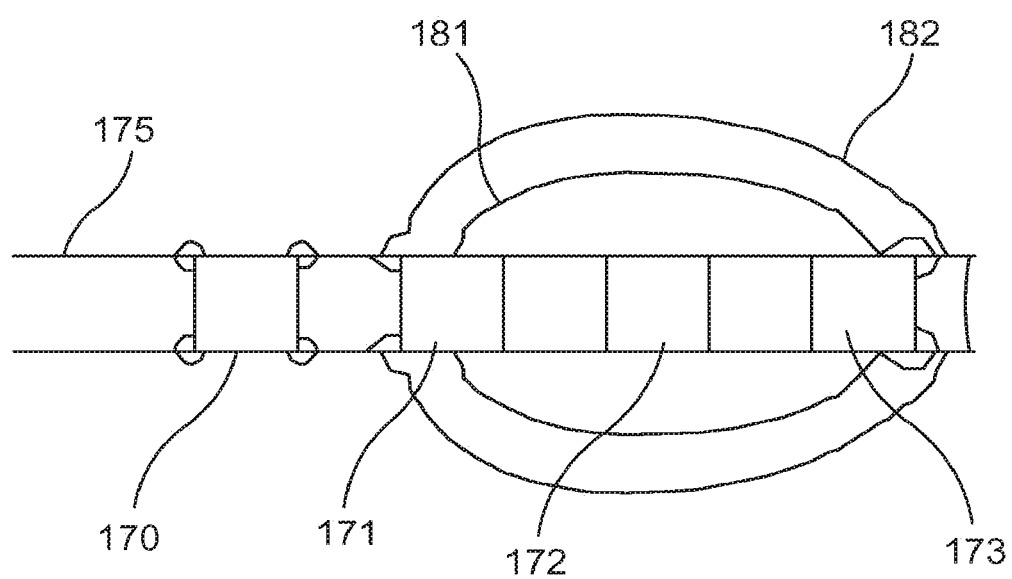
FIG. 8 is a schematic illustration of a distal portion of the catheter shown in FIG. 7, where multiple electrodes are shown along with simulation results for isomagnitude contours of electric field lines around the distal portion of the catheter.

Isomagnitude contours for electric field lines corresponding to the catheter described in the previous paragraph and depicted in FIG. 7 are illustrated in FIG. 8. As before, the catheter shaft 175 has four electrodes 170, 171, 172 and 173 disposed in its distal region. Given a set of electrode polarities and tissue/material properties, Maxwell's equations can be solved for the electric field in the region surrounding the catheter. Results from such a computational simulation are illustrated in FIG. 8, where corresponding contours of equal electric field magnitude or isomagnitude contours were generated and are shown as contours 181 and 182 in FIG. 8. It is evident that the contours bulge outward preferentially near the source electrode 172. In this manner the treatment zone may be suitably tailored or customized as desired for the procedure at hand.

Figure 9:
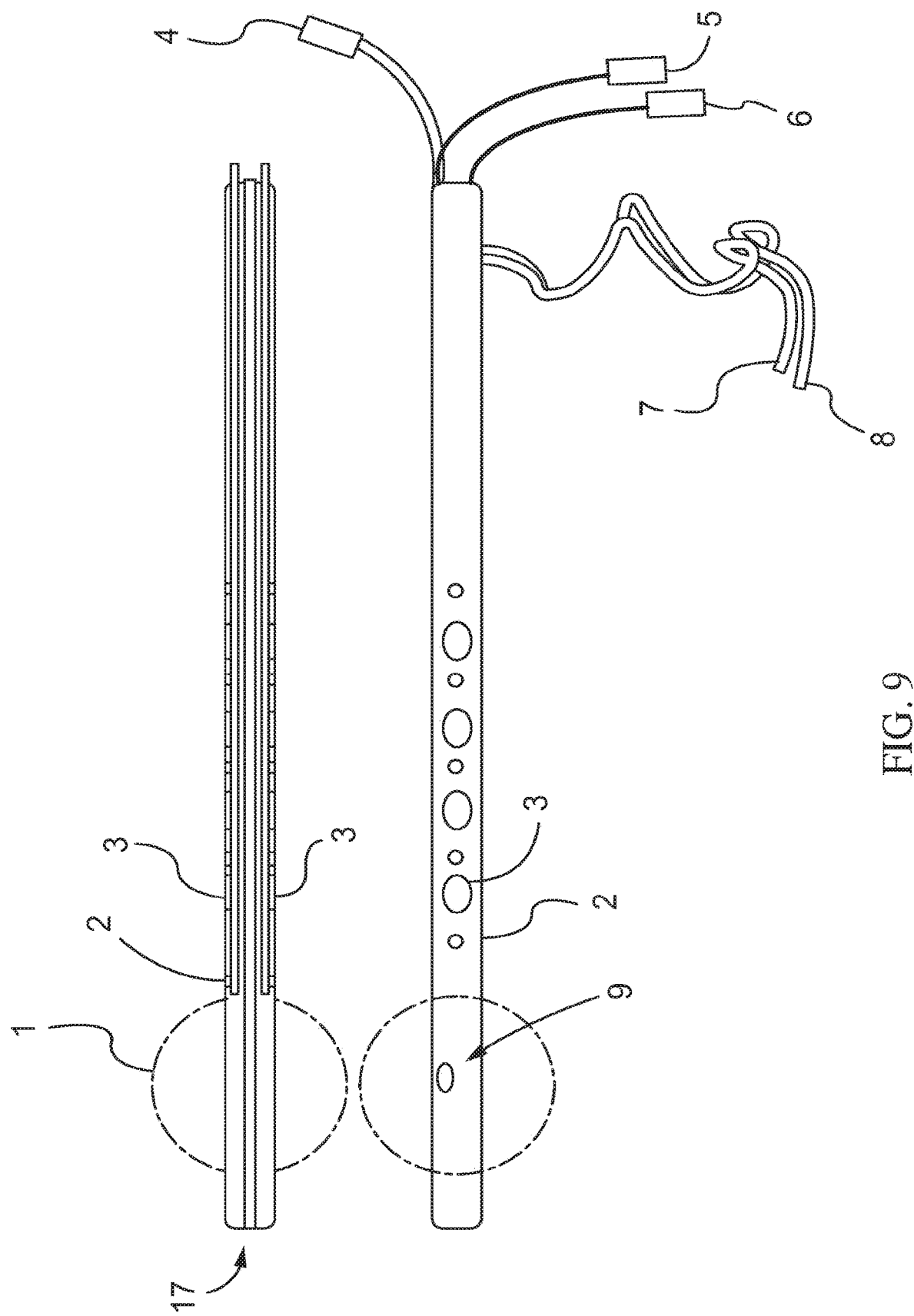
FIG. 9 is an illustration of a catheter according to an embodiment with a series of lateral ablation electrodes, lateral ports for circulation of cooling fluid, and a distal balloon for holding the catheter distal tip firmly in the bladder.

FIG. 9 is an illustration of an embodiment of an electroporation ablation catheter with a series of lateral ablation electrodes and a distal balloon. As shown in FIG. 9, the catheter has a through lumen 17 and a distal balloon 1 that is inflated from a port 4 through which for example a saline fluid is infused to expand the balloon. The catheter has a series of electrodes such as 3 arrayed in lateral pairs as shown in the top and bottom representations (rotated by 90 degrees about the catheter axis relative to each other) in FIG. 9, as well as a series of lateral ports 2 adjacent to respective electrodes. Electrodes leads 7 and 8 of opposite polarities are used to apply voltages of opposing polarities respectively on each electrode of a laterally opposing electrode pair. Proximal port 4 is used to infuse or withdraw saline or other fluid to expand or contract the distal balloon 1, while ports 5 and 6 are used for the circulation of cooling fluid (forward and backward flows). In use, the catheter is positioned in the urethra with the distal tip in the bladder; subsequently, the distal balloon is inflated, thereby holding the catheter in place within the urethra, with the region of catheter shaft with electrodes abutting prostate tissue. The through lumen 17 is used to drain the bladder as needed in the procedure. The series of electrodes on the device would be spaced with a separation between closest edges in the approximate range 1 mm to 7 mm. The catheter diameter would be approximately in the range of 2 mm; the small separation (approximately the catheter diameter) between opposing electrodes in a laterally opposed pair implies that a reduced voltage can be used to drive electroporation. The catheter shaft is constructed of flexible material such as Teflon that also has a suitably high dielectric strength.

Figure 10:
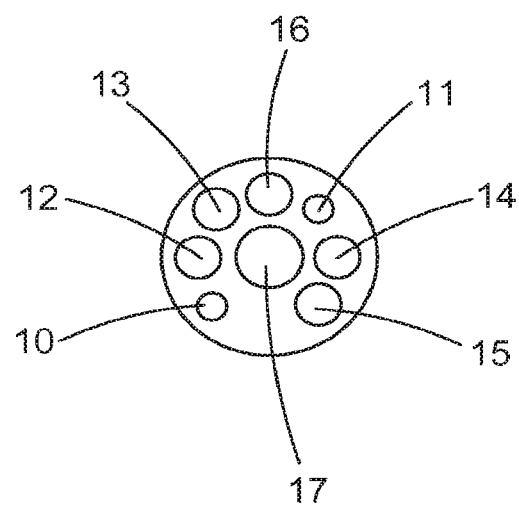
FIG. 10 is an illustration of a cross section of the shaft of the catheter shown in FIG. 9, with a multiplicity of lumens for circulation of cooling fluid, draining of the bladder, electrode leads, and distal balloon inflation.

As shown in FIG. 10, the cross section of the shaft of the catheter with lateral electrodes and lateral ports has a multiplicity of lumens. The central lumen 17 drains the bladder, while the electrode leads (of opposing polarities) pass through lumens 10 and 11. Lumen 16 carries saline or other fluid to inflate or deflate the distal balloon. Lumens 12 and 13 carry cooling fluid in one direction (forward, for example), while lumens 14 and 15 carry cooling fluid in an opposite direction (backward, for example), thereby in effect circulating cooling fluid through the lateral ports and maintaining a circulating saline pool in the urethra around the electrodes. The cooling fluid can be for example saline fluid at a temperature in the range between approximately 50 degrees Fahrenheit and 75 degrees Fahrenheit, so that it is significantly colder than normal body temperature. The cooling fluid reduces the temperature of the epithelial tissue of the urethral wall, correspondingly increasing the threshold electric field for irreversible electroporation. In this situation, the electric field generated between the lateral electrodes leaves the urethral wall tissue unaffected, while the electric field in the region of prostate tissue can drive irreversible electroporation there.

Figure 11:
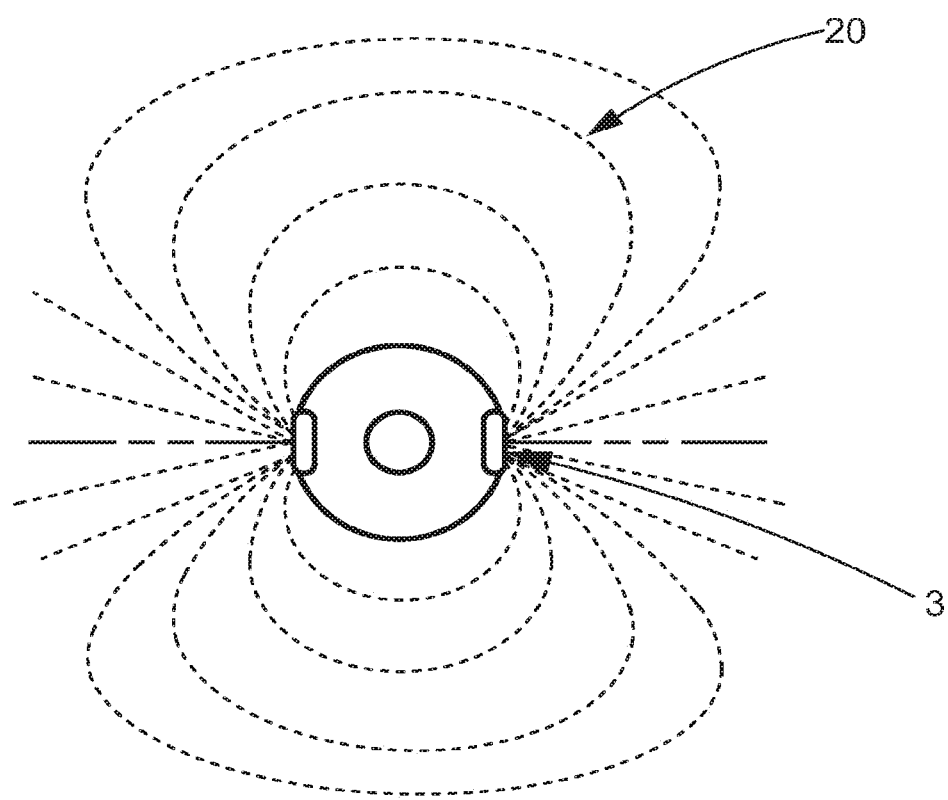
FIG. 11 is a schematic depiction of electric field lines around the cross section of a catheter according to an embodiment with a series of lateral ablation electrodes.

FIG. 11 provides a schematic depiction of electric field lines around the cross section of a catheter with a series of lateral ablation electrodes. In FIG. 11, laterally opposing electrodes 3 are shown on the left and right sides of the catheter shaft cross section, and when a voltage is applied across the lateral electrode pair, corresponding electric field lines 20 are schematically shown in the illustration.

Figure 12:
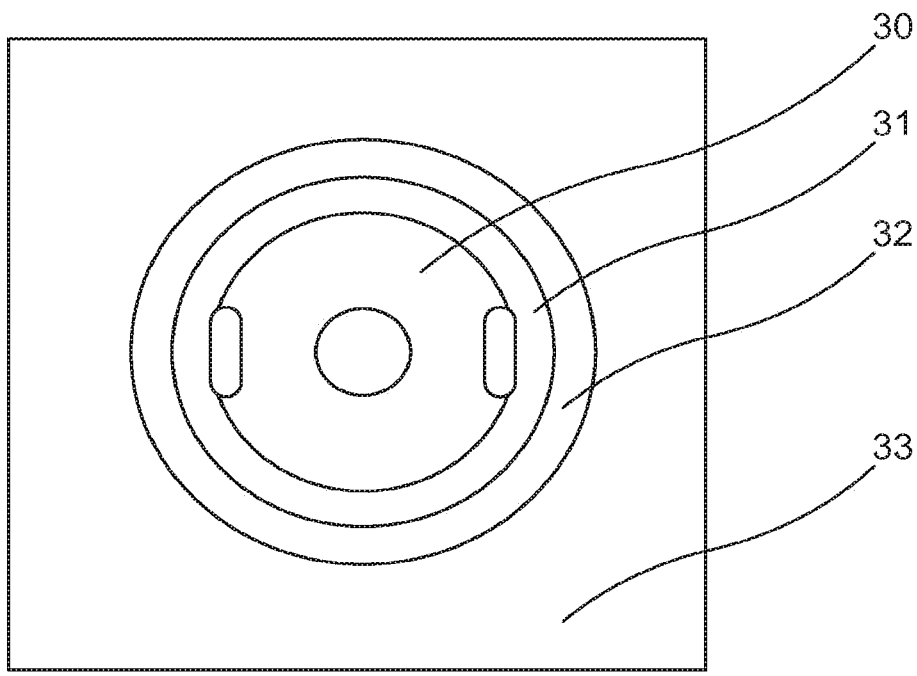
FIG. 12 is a schematic illustration of the cross section of a catheter according to an embodiment with a series of lateral ablation electrodes located within a urethra surrounded by prostate tissue, with cooling fluid infused from lateral ports filling an annular space in the urethra.

The geometry of the catheter disposed in the urethra is illustrated schematically in cross section in FIG. 12. The urethra has a urethral wall 32 and the ablation catheter 30 according to an embodiment is disposed within the urethral cross section. Cooling fluid 31 circulated through the catheter's lateral ports as described above serves to lower the temperature of the urethral wall 32 and generally forms an annular space around the catheter. The cooling fluid is delivered in brief pulses no more than approximately between 10 seconds and 40 seconds in duration, as described earlier. In this manner, while the urethral wall is rapidly cooled due to proximity with the cooling fluid during the application of electroporation voltage pulses, the prostate tissue 33 external to the urethra and just adjacent to it is not cooled very much, and is thus susceptible to irreversible electroporation by the electric field generated between the catheter electrodes. The delivery of electroporation voltage pulses is arranged to occur while the cooling fluid is in circulation to cool the urethral wall, with the delivery of cooling fluid itself occurring in flow pulses that are of a longer duration than the electroporation voltage pulses as described in the foregoing.

Figure 13:
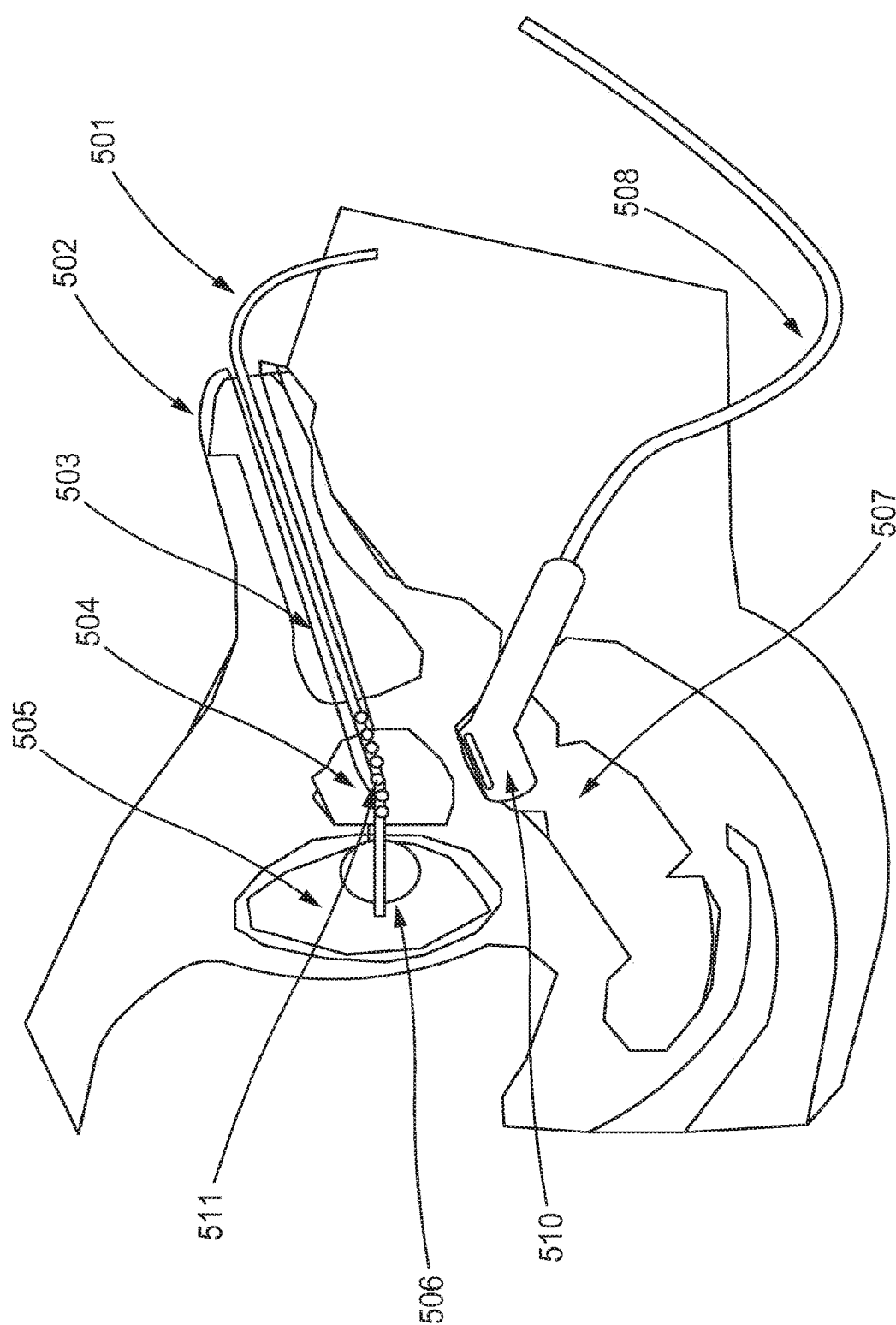
FIG. 13 is an illustration of a system for selective prostate tissue electroporation ablation according to an embodiment, including an ablation catheter with ports for cooling fluid infused into the urethra to maintain the urethral tissue lining at a relatively low temperature, and a trans-rectal probe inserted into the rectum and placed in apposition to the prostate and incorporating means for delivery of thermal energy to prostate tissue in order to maintain it at a relatively high temperature.

In some embodiments, the prostate ablation system can further include a trans-rectal probe inserted into the rectum and placed in apposition to the prostate, with the trans-rectal probe incorporating a means of thermal energy delivery for example in the form of focused ultrasound, radiant heat source, infrared source, thermoelectric heating source, or microwave source or other such means of thermal energy delivery that are known in the art. As shown in FIG. 13, the trans-rectal probe 508 is inserted into the rectum 507, and the probe has a probe head 510 incorporating means for thermal energy delivery. The prostate 504 and the bladder 505 are indicated in FIG. 13, and the trans-urethral ablation catheter 501 is inserted into the urethra 503 by access through the penis 502. The ablation catheter has a distal balloon 506 that when inflated, as shown in FIG. 13, serves to lodge the distal portion of the catheter firmly within the bladder and thus the catheter itself firmly within the urethra with the ablation electrodes indicated as dots 511 positioned adjacent to the prostate.

The rectal probe 508 heats the prostate tissue by a relatively modest amount to stay within a safe range, generating a temperature increase preferably in the range of 3 to 10 degrees Fahrenheit. This thermal energy delivery could itself be pulsed, for example in pulses lasting between approximately 10 seconds and 60 seconds, depending on the mode of thermal energy delivery and the associated specific details of heat transfer to tissue. For example, in the case where the thermal energy is delivered by focused ultrasound by means of incorporating one or more ultrasound transducers and possibly ultrasound reflectors as well thereby generating a focal spot or focal zone for ultrasound within the prostate tissue, the local tissue temperature in the focal zone can be increased quite rapidly. The local tissue heating has the effect of decreasing the irreversible electroporation threshold electric field, thus making it possible to successfully ablate prostate tissue with generated electric fields that are not too large. In this case electric field values in the range of a few hundred Volts/cm would suffice to drive irreversible electroporation in the desired treatment zone in prostate tissue, while at the same time the cooled urethral wall (cooled with cooling fluid circulated through the ablation catheter) is left intact without being ablated.

Figure 14:
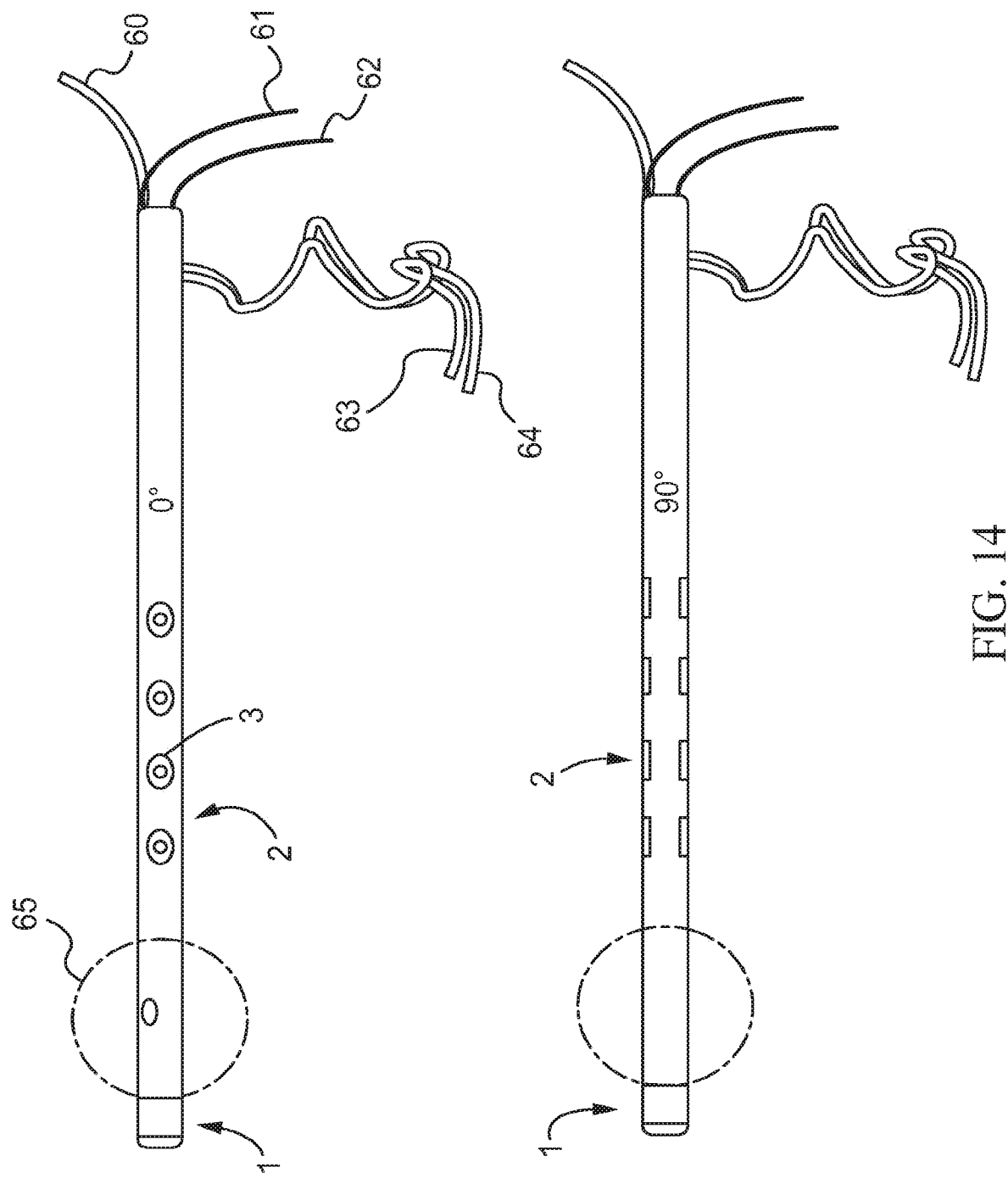
FIG. 14 is an illustration of an electroporation ablation catheter according to an embodiment, showing a series of lateral electrodes with ports incorporated for circulation of cooling fluid, and including a distal balloon and a distal tip electrode.

Several variations of ablation catheter design or embodiment can be constructed as may be convenient from a manufacturing standpoint or for procedural ease of use. In one variation illustrated in FIG. 14, two views of an ablation catheter with fluid ports co-located with electrodes are shown in the top and bottom sketches (the two views differ by a 90 degree rotation about the catheter long axis). In this construction, the ablation catheter has a distal electrode 1 and a distal balloon 65, as well as a series of laterally opposed pairs of distal electrodes 3 incorporating fluid ports 2. The series of electrodes on the device would be spaced with a separation between closest edges in the approximate range 1 mm to 7 mm. Electrode leads 63 and 64 connect to electrodes on opposite lateral sides respectively. Fluid track or tube 60 carries fluid (for example, saline) to inflate or deflate the distal balloon 65, while fluid tubes 61 and 62 can support cooling fluid circulation flow in opposite directions (for example, forward and backward respectively). The lateral fluid ports permit the circulation of cooling fluid; thus cooling fluid exits the ports on one side of the catheter (for example, the left side of the catheter as seen looking down from the distal end) and enters the ports on the opposite side of the catheter (for example, the right side of the catheter as seen looking down from the distal end). In this manner the annular space between the catheter and the inner wall of the urethra is filled with cooling fluid along the portion of the catheter shaft with the electrodes and fluid ports. Furthermore, the catheter can possibly incorporate a through lumen for evacuation or draining of the bladder.

Figure 15:
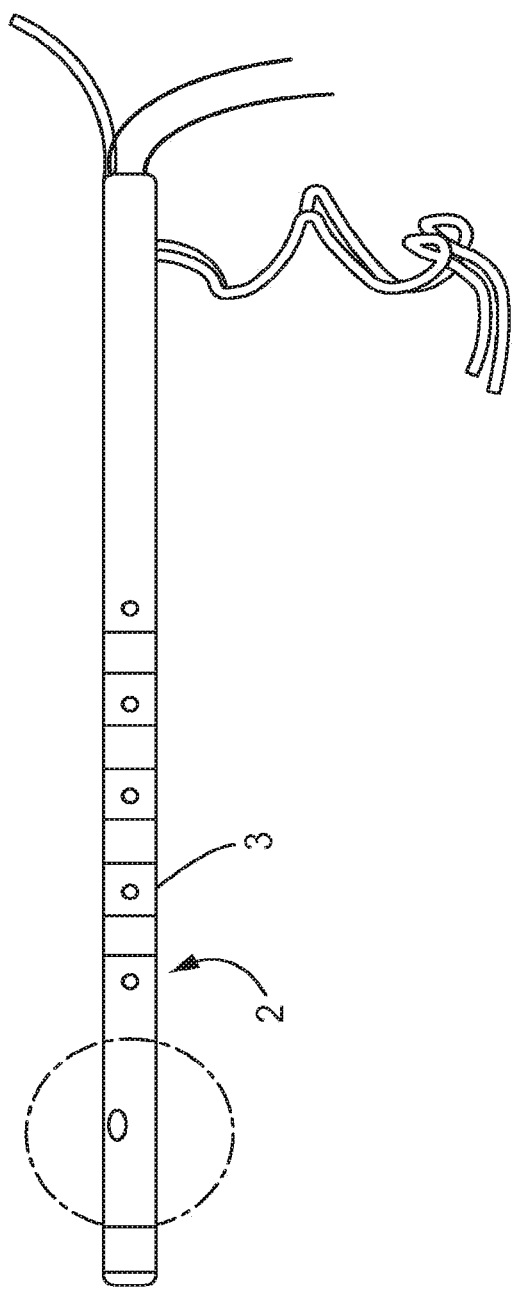
FIG. 15 is an illustration of an electroporation ablation catheter according to an embodiment, showing a series of ring electrodes, a series of lateral ports, and including a distal balloon and a distal tip electrode.
Figure 16:
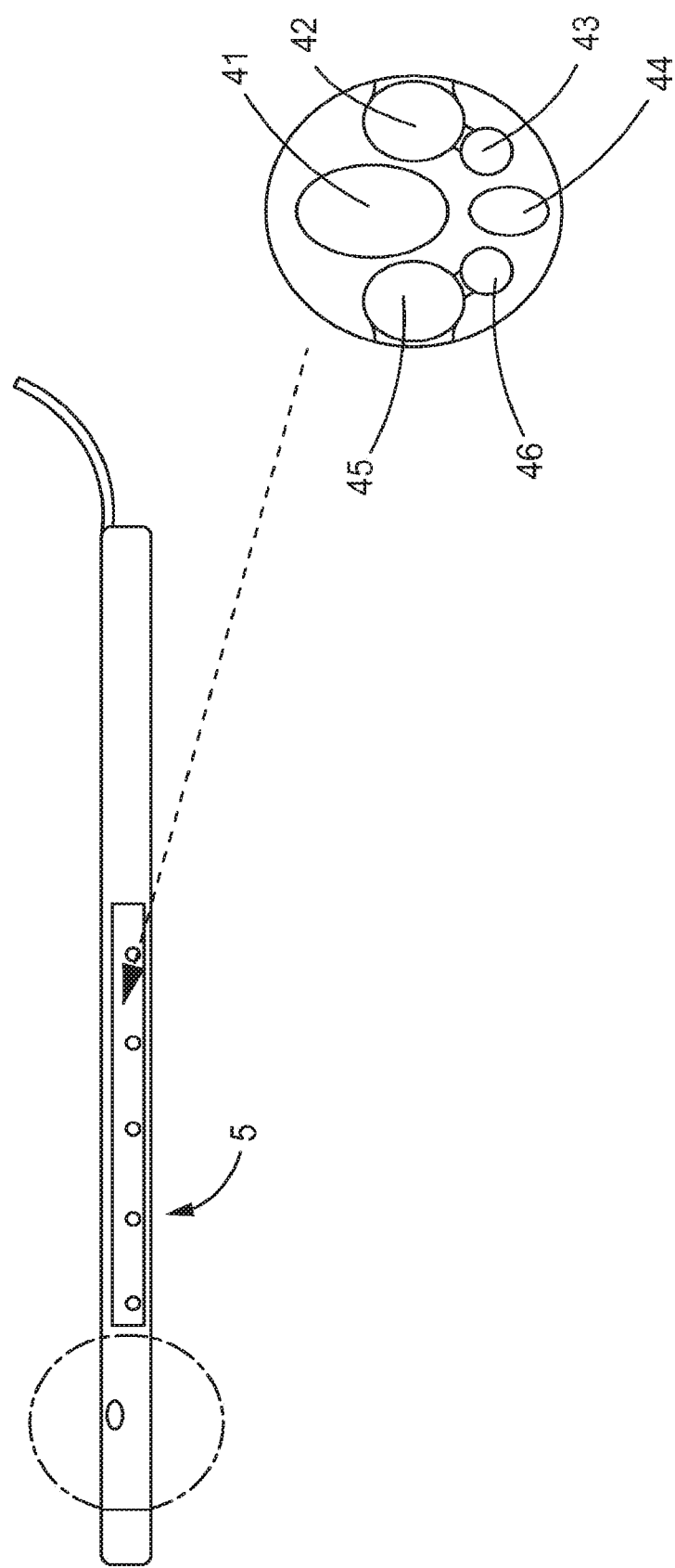
FIG. 16 is an illustration of an electroporation ablation catheter according to an embodiment with a series of ring electrodes, lateral ports for cooling fluid circulation and a distal tip electrode, showing a cut-away cross section view of the catheter shaft, and including a multiplicity of lumens for circulation of cooling fluid, draining of the bladder, electrode leads, and distal balloon inflation.

In another alternate embodiment of the ablation catheter according to an embodiment, as shown in FIG. 15, the catheter can have a distal tip electrode and a distal balloon, as well as a series of ring electrodes 3 and lateral fluid ports 2 disposed along a distal portion of the catheter shaft. The lateral fluid ports are used for circulation of cooling fluid, as described in the foregoing, while the ring electrodes and the tip electrode are used to generate an electric field for ablation with suitable voltage pulses, as described above. The series of electrodes on the device would be spaced with a separation between closest edges in the approximate range 1 mm to 7 mm. FIG. 16 shows a cut-away view of such a catheter where fluid ports 5 are visible from the inside of the shaft, while the cross-section view provided illustrates a set or multiplicity of lumens. A central lumen 41 serves to drain the bladder, while lumens 43 and 46 are cooling fluid irrigation lumens carrying fluid flow in opposite directions (for example, forward and backward respectively). Lumen 44 carries fluid to inflate or deflate the distal balloon, while lumens 42 and 45 act as passages for electrode leads of opposite polarities respectively and possibly also for cooling fluid irrigation/circulation.

Figure 17:
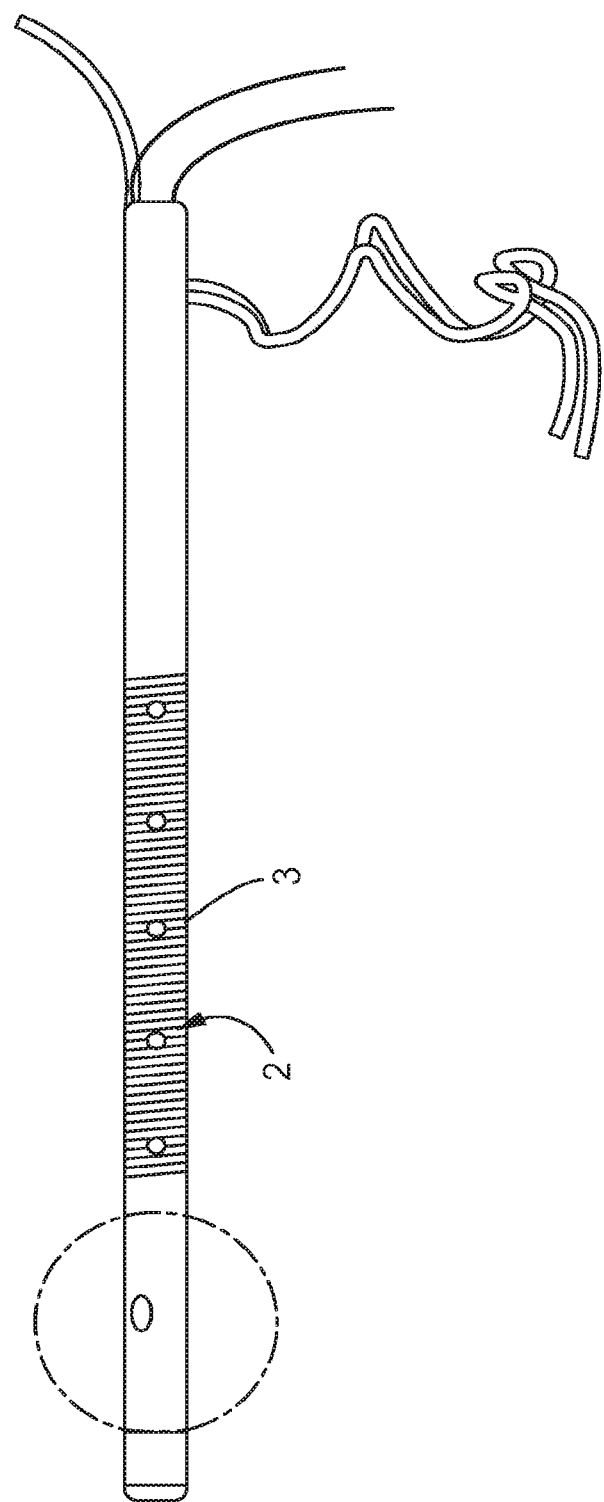
FIG. 17 is an illustration of an electroporation ablation catheter according to an embodiment, showing a long flexible electrode, a series of lateral ports, and including a distal balloon and a distal tip electrode.
Figure 18:
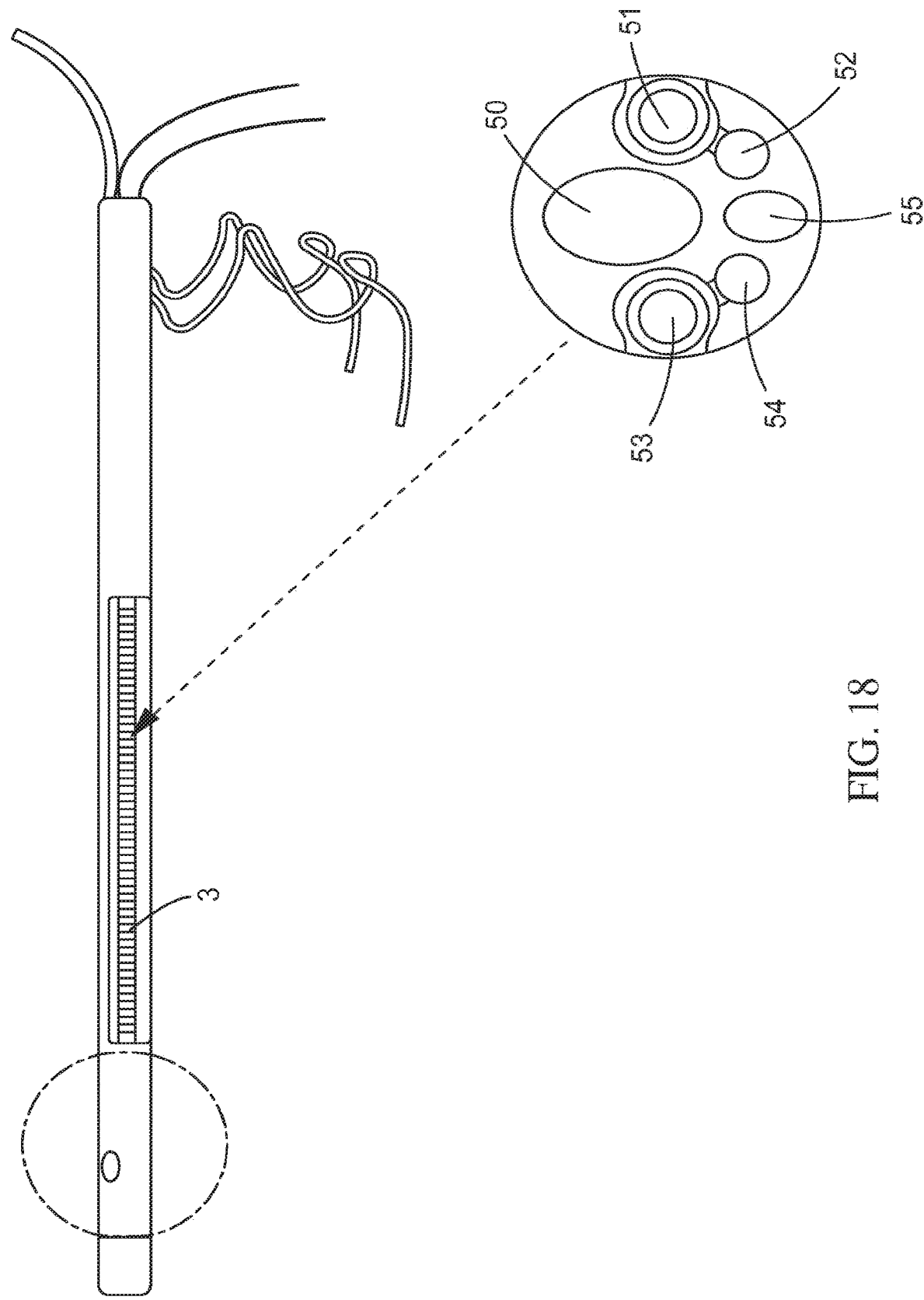
FIG. 18 is an illustration of an electroporation ablation catheter according to an embodiment, with a long flexible electrode, lateral ports for cooling fluid circulation and a distal tip electrode, showing a cut-away cross section view of the catheter shaft, and including a multiplicity of lumens for circulation of cooling fluid, draining of the bladder, electrode leads, and distal balloon inflation.

In yet another alternate embodiment, the ablation catheter can have, as illustrated in FIG. 17, a distal tip electrode, a distal balloon, a long flexible electrode 3 (for example, in the form of a long helical winding of metallic composition) and a set of lateral ports 2 on either side of the catheter for circulation of cooling fluid. The series of lateral ports on the device would be spaced with a separation between closest edges in the approximate range 1 mm to 7 mm. As shown in the cut-away view of such a catheter in FIG. 18, fluid ports 3 are visible from the inside of the shaft, while the cross-section view provided illustrates a set or multiplicity of lumens. A central lumen 50 serves to drain the bladder, while lumens 52 and 54 are cooling fluid irrigation lumens carrying fluid flow in opposite directions (for example, forward and backward respectively). Lumen 55 carries fluid to inflate or deflate the distal balloon, while lumens 51 and 53 act as passages for electrode leads of opposite polarities respectively and possibly also for cooling fluid irrigation/circulation.

Figure 19:
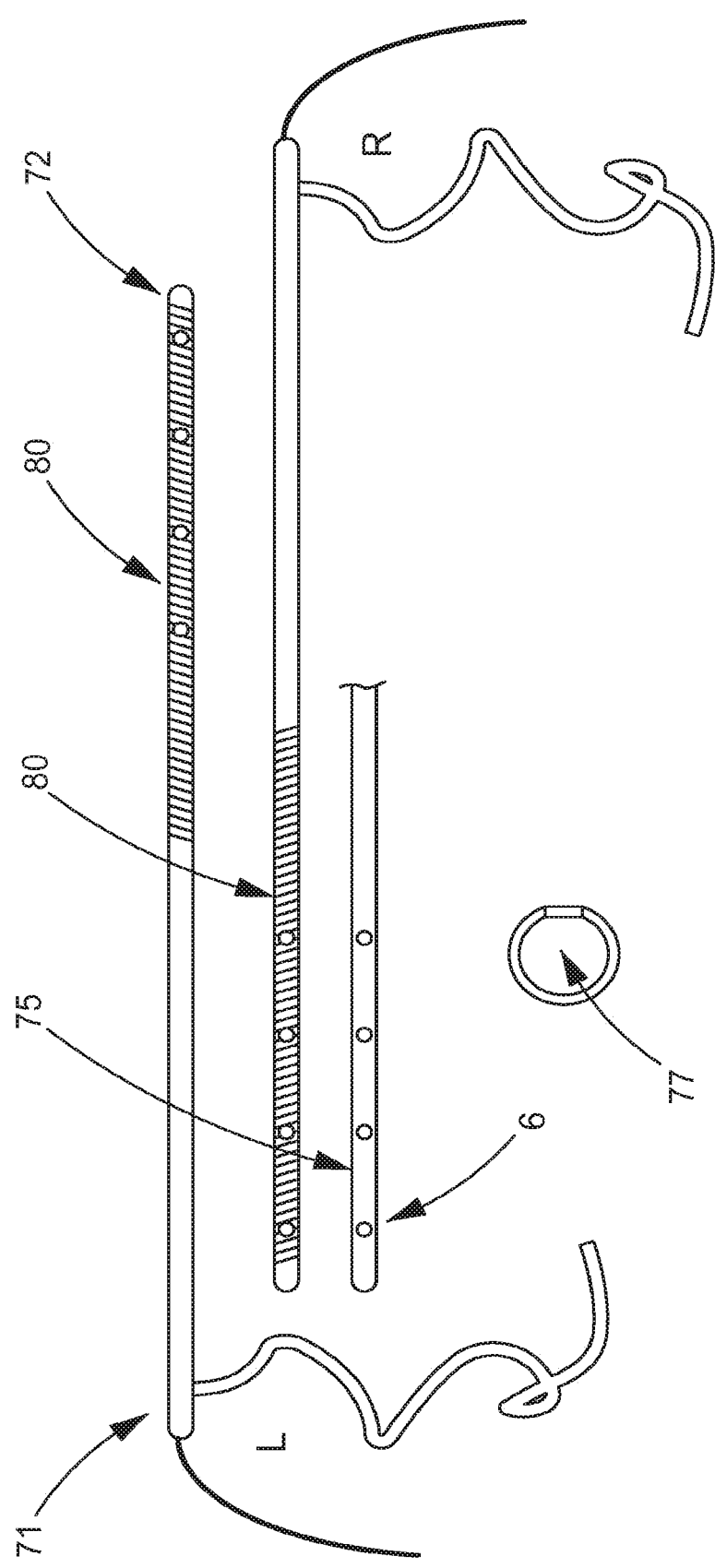
FIG. 19 is an illustration of left and right lateral views of an electroporation ablation catheter according to an embodiment with a long flexible electrode and a series of lateral ports.

In still another alternate embodiment of ablation catheter shown in FIG. 19, left and right views of a catheter with proximal end 71 and distal end 72 are both shown for clarity (left and right views are marked L and R respectively), the catheter having a long flexible electrode 80 and lateral ports 6 for cooling fluid irrigation through the irrigation shaft 75 with lumen 77 for fluid irrigation as well as electrode leads. The distal electrode is not marked.

Figure 20:
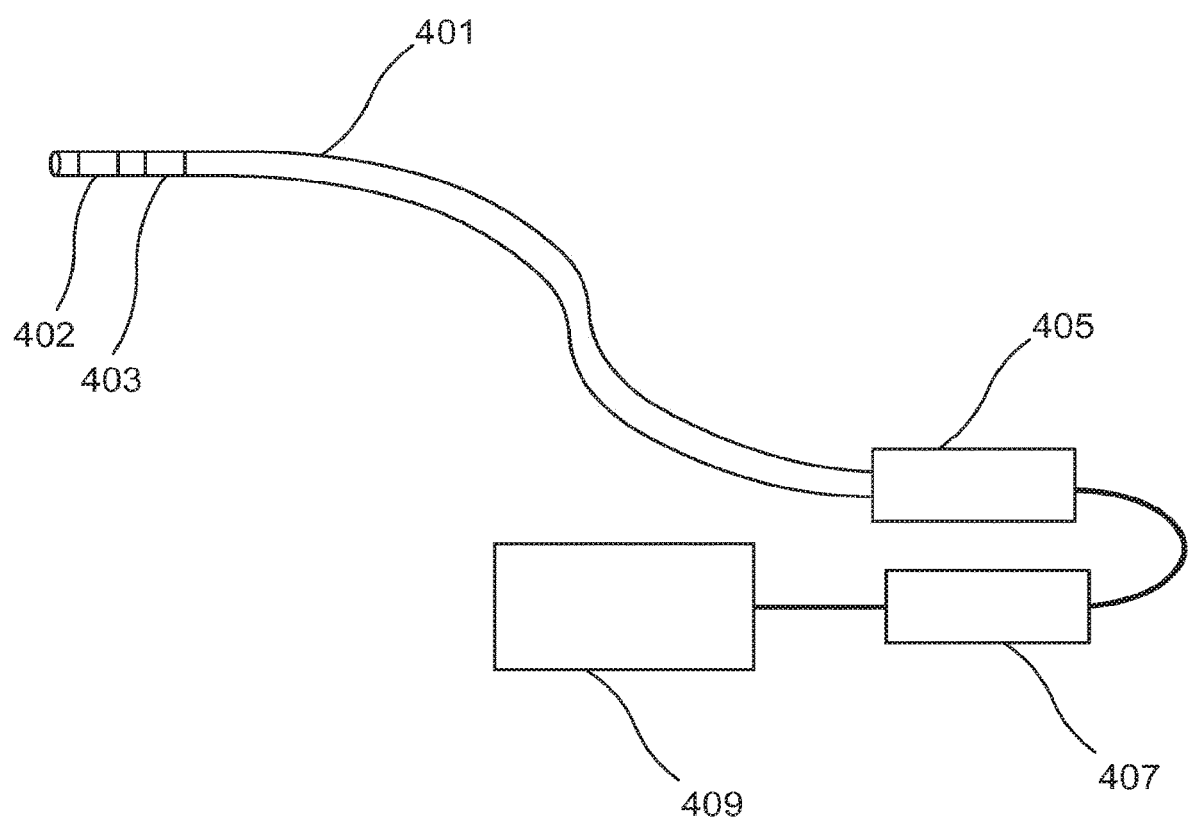
FIG. 20 is a schematic illustration of a device and electroporation system according to an embodiment for transurethral ablation with a defibrillator voltage input.

In the embodiments with a distal electrode, while the distal electrode can generally be either an anode or a cathode, in some embodiments it is a cathode, since this can reduce the likelihood of flash arcing. The various embodiments of ablation catheters described above can be used in Trans-Urethral Rectoscopy Procedures (TURP), where the tissue resection is performed by irreversible electroporation ablation. In such an application, as shown in FIG. 20, an ablation catheter device 401 with multiple electrodes is shown (two electrodes 402 and 403 marked in its distal portion are shown for schematic illustration purposes). The catheter in this embodiment can be connected to a pulse generator 409 in the form of a defibrillator unit, which could possibly be a standard commercial unit such as a Booker Box. The catheter can incorporate an IGBT switch, possibly disposed in the catheter handle 405. In some embodiments, the switch can even be mounted in a disposable unit or box 407 that connects to the catheter handle and interfaces with the defibrillator unit. In an alternate embodiment, the switch can be incorporated in the catheter handle. The switch unit is designed to operate in pulsed fashion so that for example only a discrete time interval of pulse, for example 700 microseconds of defibrillator output, is passed through the catheter in a set of discrete pulses. The switch unit also is capable of accepting a variety of DC voltage sources, and has an in-built shunt circuit to shed or shunt away excess current. In this manner, even a standard defibrillator could be used with the ablation catheter device described herein to generate irreversible electroporation. In particular, the ablation catheter device can be very beneficial in Trans-Urethral clinical applications such as TURP.

Figure 21:
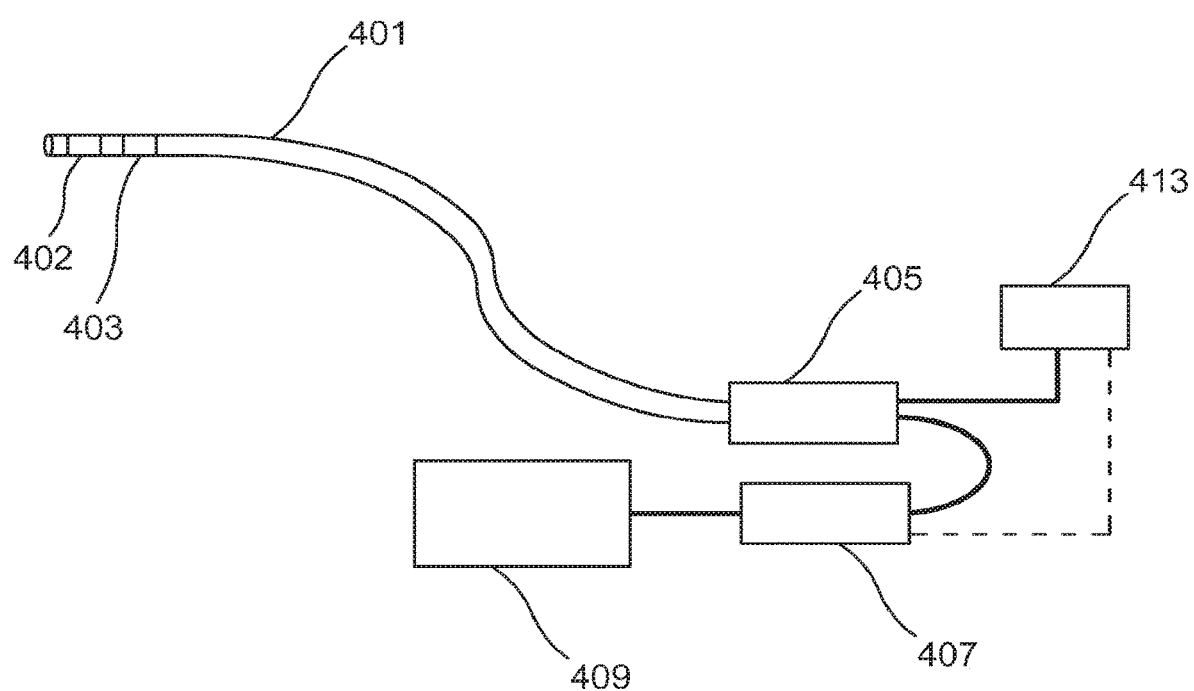
FIG. 21 is a schematic illustration of a device and electroporation system according to an embodiment for transurethral ablation with a defibrillator voltage input and a cooled fluid pump for pumping cold fluid through the device.

As shown in FIG. 21, in some embodiments the catheter handle 405 can further be connected to a fluid pump 413 capable of pumping cooled fluid such as cooled saline through the catheter. Preferably the pump is capable of delivering and controlling pulsatile fluid flow wherein the fluid is delivered in pulses. In one embodiment the saline pump can deliver either cooled or heated or warmed fluid, while in another embodiment the saline pump can deliver cooled fluid while a trans-rectal probe with a means of inducing heating of prostate tissue is also used in the procedure. As indicated by the dashed lines between switch unit 407 and fluid pump 413, the switch unit can also drive control signals to the pump for setting fluid pulse control parameters such as fluid temperature and flow. Furthermore, when the ablation catheter is used in conjunction with a trans-rectal probe, the switch unit is capable of suitably timing or coordinating the delivery of cooling fluid through the catheter and thermal energy delivery via the rectal probe. In some embodiments the thermal energy delivery from the rectal probe is also performed in pulsed fashion.

In an alternate embodiment, instead of a defibrillator unit, the signal generator box 409 could comprise a programmable pulse generator of the types previously described herein. In a further alternate embodiment, such programmability (for example, of electrode selection) can be made from the switch unit 407, possibly through connection to a computer or other user interface. Further, in one embodiment sensed temperature data from the distal portion of the medical device (from a thermistor or thermocouple, for example) can be used to adjust the temperature of the saline fluid flow.

While various specific examples and embodiments of systems and tools for selective tissue ablation with irreversible electroporation were described in the foregoing for illustrative and exemplary purposes, it should be clear that a wide variety of variations and alternate embodiments could be conceived or constructed by those skilled in the art based on the teachings according to an embodiment. While specific methods of control and DC voltage application from a generator capable of selective excitation of sets of electrodes were disclosed, persons skilled in the art would recognize that any of a wide variety of other control or user input methods and methods of electrode subset selection etc. can be implemented without departing from the scope according to an embodiment. Likewise, while the foregoing described a range of specific tools or devices for more effective and selective DC voltage application for irreversible electroporation through fluid irrigation and catheter devices, other device constructions or variations could be implemented by one skilled in the art by employing the principles and teachings disclosed herein without departing from the scope according to an embodiment in a variety of medical applications.

Furthermore, while the present disclosure describes specific embodiments and tools involving irrigation with saline fluids and the use of temperature to selectively ablate tissue by taking advantage of the temperature-dependence of the threshold of irreversible electroporation, it should be clear to one skilled in the art that a variety of methods and devices for steady or pulsed fluid delivery, or for tissue or electrode cooling, or thermal energy delivery via a trans-rectal probe, could be implemented utilizing the methods and principles taught herein without departing from the scope according to an embodiment.

Accordingly, while many variations of methods and tools disclosed here can be constructed, the scope according to an embodiment is limited only by the appended claims.

The invention claimed is:

1. A method, comprising:
  receiving, at an electrode controller, a temperature signal associated with a first portion of tissue near a catheter, the catheter including a plurality of electrodes;
  delivering, by the electrode controller, one or more control signals based on the temperature signal to at least one of:
    a cooling unit configured to deliver a cooling fluid to the catheter to cool the first portion of tissue; or
    a heater configured to heat a second portion of tissue; and
  delivering, by the electrode controller, an output signal associated with a pulsed voltage waveform to the plurality of electrodes, the electrode controller operatively coupled to a voltage pulse generator configured to produce the pulsed voltage waveform.

2. The method of claim 1, further comprising:
shunting, by the electrode controller, an excess current associated with the pulsed voltage waveform.

3. The method of claim 1, further comprising:
selecting, by the electrode controller, at least a first electrode from the plurality of electrodes and a second electrode from the plurality of electrodes,
the delivering the output signal associated with the pulsed voltage waveform to the plurality of electrodes including delivering the output signal associated with the pulsed voltage waveform to the to the first electrode and the second electrode.

4. The method of claim 1, further comprising:
modulating, by the electrode controller, a characteristic of the output signal, the characteristic including at least one of: an amplitude of the output signal, a period of the output signal, or a duration of the output signal.

5. The method of claim 1, further comprising:
producing, by the electrode controller, the output signal by incorporating intervals with zero voltage into voltage pulses from the voltage pulse generator.

6. The method of claim 1, further comprising:
interfacing, by the electrode controller, with an external device to program at least one of an amplitude of the output signal, a period of the output signal, or a duration of the output signal.

7. The method of claim 1, wherein the one or more control signals is configured to control at least one of a flow of the cooling fluid or a temperature of the cooling fluid.

8. The method of claim 1, wherein the delivering the output signal associated with the pulsed voltage waveform occurs when the temperature of the first portion of tissue is maintained below a body temperature.

9. The method of claim 1, wherein the heater is an ultrasound heater, and the one or more control signals is configured to control a characteristic of ultrasound energy produced by the ultrasound heater.

10. The method of claim 1, wherein the heater is an infrared heater, and the one or more control signals is configured to control a characteristic of infrared energy produced by the infrared heater.

11. The method of claim 1, wherein the output signal is in a range between about 200 and about 400 Volts.

12. The method of claim 1, wherein the catheter further includes an expandable member, the method further comprising:
producing, by an inflation controller operatively coupled to the catheter, an inflation signal to control delivery of an inflation fluid to the expandable member.

13. The method of claim 1, wherein the first portion of tissue includes a urethral wall, and the second portion of tissue includes a portion of prostate tissue, and the catheter is positionable within a urethra such that the plurality of electrodes, in response to receiving the output signal, generates a pulsed electric field to ablate the portion of the prostate tissue while not ablating the urethral wall.

14. A method, comprising:
delivering, by a cooling unit operatively coupled to a catheter including a plurality of electrodes, a flow of cooling fluid to the catheter to cool an urethral wall, the catheter positionable within an urethra;
heating, by a heater, a portion of prostate tissue;
producing, by a voltage pulse generator, a pulsed voltage waveform; and
delivering, by an electrode controller operatively coupled to the voltage pulse generator and the catheter, an output signal associated with the pulsed voltage waveform to the plurality of electrodes such that the plurality of electrodes ablates the portion of the prostate tissue while leaving the urethral wall intact.

15. The method of claim 14, further comprising:
producing, by the heater, a focused ultrasound energy pulse for heating the portion of the prostate tissue.

16. The method of claim 14, further comprising:
producing, by the heater, an infrared energy pulse for heating the portion of the prostate tissue.

17. The method of claim 14, wherein the catheter includes an expandable member, the method further comprising:
delivering, by an inflation controller, an inflation fluid to the catheter to expand the expandable member such that the catheter is held in place within the urethra by the expandable member.

18. The method of claim 14, further comprising:
shunting, by a shunt circuit operatively coupled to the catheter, an excess current associated with the pulsed voltage waveform.

19. The method of claim 14, wherein the delivering the output signal includes:
switching between delivering the output signal to subsets of electrodes of the plurality of electrodes.

20. The method of claim 14, further comprising:
modulating, by the electrode controller, a characteristic of the output signal, the characteristic including at least one of: an amplitude of the output signal, a period of the output signal, or a duration of the output signal.

\* \* \* \* \*